(12) United States Patent
Lawman et al.

(10) Patent No.: US 6,986,887 B2
(45) Date of Patent: Jan. 17, 2006

(54) UNIVERSAL STEM CELLS

(75) Inventors: Patricia Lawman, Chipley, FL (US); Michael J. P. Lawman, Chipley, FL (US)

(73) Assignee: Morphogenesis, Inc., Oldsmar, FL (US)

( * ) Notice: Subject to any disclaimer, the term of this patent is extended or adjusted under 35 U.S.C. 154(b) by 68 days.

(21) Appl. No.: 10/186,231

(22) Filed: Jun. 28, 2002

(65) Prior Publication Data
US 2003/0101465 A1   May 29, 2003

Related U.S. Application Data

(63) Continuation of application No. 09/047,769, filed on Mar. 25, 1998, now abandoned.

(60) Provisional application No. 60/042,358, filed on Mar. 25, 1997.

(51) Int. Cl.
*A01N 63/00* (2006.01)
*C12N 15/00* (2006.01)
*C12N 5/00* (2006.01)
*C12N 15/63* (2006.01)

(52) U.S. Cl. ............... 424/93.21; 424/93.2; 435/320.1; 435/325; 435/455

(58) Field of Classification Search ............. 435/320.1, 435/325, 455; 424/93.2, 93.21
See application file for complete search history.

(56) References Cited

U.S. PATENT DOCUMENTS

| 5,486,359 | A |   | 1/1996  | Caplan et al.     |         |
|-----------|---|---|---------|-------------------|---------|
| 5,574,205 | A | * | 11/1996 | Kucherlapati et al. | 800/3 |
| 5,679,340 | A |   | 10/1997 | Chappel           |         |
| 6,030,833 | A | * | 2/2000  | Seebach et al.    | 435/325 |

FOREIGN PATENT DOCUMENTS

| WO | WO 95/26741 A1 | 10/1995 |
|----|---------------|---------|
| WO | WO 92/22362 A1 | 7/1996  |

OTHER PUBLICATIONS

Bradley et al., 1992, Biotechnology, vol. 10, p. 534-539.*
Houdebine, L-M, 1994, Journal of Biotechnology, vol. 34, p. 269-287.*
Brenneman et al., 1996, Proc. Natl. Acad. Sci., vol. 93, pp. 3608-3612.*
Ellis et al., 2001, PNAS, vol. 98, No. 12, p. 6742-6746.*
Dyer et al., 1992, Transplantation Proceedings, vol. 24, No. 6, p. 2454.*
Cosgrove et al., 1991, Cell, vol. 66, p. 1051-1066.*
Leonard et al., 1995, Immunological Reviews, vol. 148, pp. 97-114.*
Sigmund, C., Jun. 2000, Arterioscler. Thromb. Vasc. Biol., p. 1425-1429.*
Houdebine, L-M., 2002, Journal of Biotechnology, vol. 98, p. 145-160.*
Eck et al., 1996, Goodman & Gilman's The Pharmacological Basis of Therapeutics, McGraw-Hill, New York, p. 77-101.*
Gorecki, D., 2001, Expert Opin. Emerging Drugs, 6(2): 187-198.*
Armstrong, J. W. et al. "Class I and class II major histocompatibility molecules play a role in bone marrow-derived macrophage development" *Journal of Leukocyte Biology*, 1994, pp. 658-661, vol. 55.
Auchincloss, H. "Xenogeneic Transplantation" *Transplantation*, 1988, pp. 1-20, vol. 46.
Benichou, G. et al. "Indirect T-cell allorecognition: perspectives for peptide-based therapy in transplantation" *Immunology Today*, 1997, pp. 67-71, vol. 18, No. 2.
Bidwell, J. "Advances in DNA-based HLA-typing methods" *Immunology Today*, 1994, pp. 303-307, vol. 15, No. 7.
Bradley, A. et al. "Formation of germ-line chimaeras from embryo-derived teratocarcinoma cell lines" *Nature*, 1984, pp. 255-256, vol. 309.
Capecchi, M. R. "Targeted Gene Replacement" *Scientific American*, 1994, pp. 52-59, vol. 3.
Carlow, D. A. et al. "Class I ($H-2K^b$) gene transfection reduces susceptibility of YAC-1 lymphoma targets to natural killer cells" *Eur. J. Immunol.*, 1990, pp. 841-846, vol. 20.
David-Watine, B. et al. (1990) "The regulation and expression of MHC class I genes" *Immunology Today.*, 1990, pp. 286-292, vol. 11, No. 8.
Drezen, J. M. et al. "Different regulation of class I gene expression in the adult mouse and during development" *J. Immunol.*, 1992, pp. 429-437, vol. 149.
Evans, M. J. et al. "Establishment in culture of pluripotential cells from mouse embryos" *Nature*, 1981, pp. 154-156, vol. 292.
Faustman, D., Coe, C. "Prevention of Xenograft Rejection by Masking Donor HLA Class I Antigens" *Science*, 1991, pp. 1700-1702, vol. 252.

(Continued)

*Primary Examiner*—Shin-Lin Chen
(74) *Attorney, Agent, or Firm*—Edwards & Angell, LLP

(57) ABSTRACT

The subject invention pertains to materials and methods for preparing multi-potential stem cells having a pre-selected expression of MHC antigens. Stem cells of the subject invention can be used to generate histocompatible tissues/organs for transplantation. The process of the subject invention comprises the use of targeting vectors capable of gene knockout, insertion of site-specific recombination cassettes, and the replacement of histocompatibility alleles in the stem cell. Novel knockout vectors are used to delete designated regions of one chromosome. Recombination cassette vectors are then used to delete the same region on the second chromosome and deposit a site-specific recombination cassette which can be utilized by replacement vectors for inserting the new MHC genes on the chromosome of the engineered cell. The subject invention also pertains to cells, tissues, and transgenic mammal prepared using the methods and materials of the invention.

12 Claims, 6 Drawing Sheets

OTHER PUBLICATIONS

Faustman, D. "Strategies for circumventing transplant rejection: modification of cells, tissues and organs" *Trends in Biochem. Tech.*, 1995, pp. 100-105, vol. 13.

Galli-Taliadoros, L. A. et al. "Gene knock-out technology: a methodological overview for the interested novice" *J. Immunol. Methods*, 1995, pp. 1-15, vol. 181.

Goss, J. A. et al. "Intrathymic injection of donor alloantigens induces specific tolerance to cardiac allografts" *Transplantation*, 1993, pp. 166-173, vol. 56.

Isobe, M. et al. (1992) "Specific Acceptance of Cardiac Allograft After Treatment with Antibodies to ICAM-1 and LFA-1" *Science*, 1992, pp. 1125-1127, vol. 255.

Joyner, A. J. et al. "Production of a mutation in mouse En-2 gene by homologous recombination in embryonic stem cells" *Nature*, 1989, pp. 153-156, vol. 338.

Karre, K. et al. "Selective rejection of H-2-deficient lymphoma variants suggests alternative immune defence strategy" *Nature*, 1986, pp. 675-678, vol. 319.

Kim, M. et al. "Divergent Effects of H-2K and H-2D Genes on Sensitivity of BL6 Melanoma Cells to NK Cells or TNF-Mediated Cytotoxicity" *Cellular Immunology*, 1994, pp. 358-371, vol. 155.

Lechler, R. I. et al. "Restoration of immunogenicity to passenger cell-depleted kidney allografts by the addition of donor strain dendritic cells" *J. Exp. Med.*, 1982, pp. 31-41, vol. 155.

Markmann, J. F. et al. (1994) "Genetically engineered grafts to study xenoimmunity: A role for indirect antigen presentation in the destruction of major histocompatibility complex antigen deficient xenografts" *Surgery*, 1994, pp. 242-249, vol. 116, No. 2.

Mansour, S. L. et al. "Disruption of the proto-oncogene int-2 in mouse embryo-derived stem cells: a general strategy for targeting mutations to non-selectable genes" *Nature*, 1988, pp. 348-352, vol. 336.

Pearson, T. C. et al. "Induction of transplantation tolerance in adults using donor antigen and anti-CD4 monoclonal antibody" *Transplantation*, 1992, pp. 475-483, vol. 54, No. 3.

Schwartzberg, P. L. et al. "Germ-Line Transmission of a c-abl Mutation Produced by Targeted Gene Disruption in ES Cells" *Science*, 1989, pp. 799-803, vol. 246.

Shim, H. et al. "Isolation of Pluripotent Stem Cells from Cultured Porcine Primordial Germ Cells" *Biology of Reproduction*, 1997, pp. 1089-1095, vol. 57.

Siebers U., et al., "Bioartificial Pancreas: Islet Survival and Interleukin-1 Action" *Transplantation Proceedings*, 1990, pp. 2035-2036, vol. 22, No. 4.

Smithies, O. et al. "Insertion of DNA sequences into the human chromosomal β-globin locus by homologous recombination" *Nature*, 1985, pp. 230-234, vol. 317.

Stange, J. et al. "Hepatocyte encapsulation—initial intentions and new aspects for its use in bioartificial liver support" *The International Journal of Artificial Organs*, 1996, pp. 45-48, vol. 19.

Te Riele, H. et al. "Highly efficient gene targeting in embryonic stem cells through homologous recombination with isogenic DNA constructs" *Proc. Natl. Acad. Sci.*, 1992, pp. 5128-5132, vol. 89.

Thomas, K. R. et al. (1987) "Site-Directed Mutagenesis by Gene Targeting in Mouse Embryo-Derived Stem Cells" *Cell*, 1987, pp. 503-512, vol. 51.

Wong, W. "Syngeneic bone marrow expressing a single donor class I MHC molecule permits acceptance of a fully allogenic cardiac allograft" *Transplantation*, 1996, pp. 1462-1468, vol. 62.

Pursel, V. G. et al. "Expression and performance in transient pigs" *J. Reprod. Fert. Suppl.*, 1990, pp. 235-245, vol. 40.

Palmiter, R. D. et al. "Mettallothionein-human GH fusion genes stimulate growth of mice" *Science*, 1983, pp. 809-814, vol. 222.

Houdebine, L.-M. "Production of pharmaceutical proteins from transient animals" *Journal of Biotechnology*, 1994, pp. 269-287, vol. 34.

Bradley, A. et al. "Modifying the mouse: Design and desire" *Bio/Technology*, 1992, pp. 534-539, vol. 10.

Seamark, R. F. "Progress and emerging problems in livestock transgenesis: a summary perspective" *Reprod. Fertil. Dev.*, 1994, pp. 653-657, vol. 6.

Kappel, C. A. et al. "Regulating gene expression in transgenic animals" *Current Opinion in Biotechnology*, 1992, pp. 548-553, vol. 3.

Hammer, R. E. et al. "Genetic Engineering of Mammalian Embryos" *Journal Animal Sci.*, 1986, pp. 269-278, vol. 63.

Sasazuki et al. "Effect of matching of class I HLA alleles on clinical outcome after transplantation of hematopoietic stem cells from an unrelated donor" *New England J. of Med.*, 1998, pp. 1177-1185, vol. 338, No. 17.

Egea, G. E. et al. "Association of polymorphisms in the HLA-B region with extended haplotypes" *Immunogenetics*, 1991, pp. 4-11, vol. 33, No. 1.

Prockop, D. J. et al. "Marrow stromal cells as stem cells for nonhematopoietic tissues" *Science*, 1997, pp. 71-74, vol. 276.

Gerson, S. L. et al. "Mesenchymal stem cells: No longer second class marrow citizens" *Nature Medicine*, 1999, pp. 262-264, vol. 53, No. 3.

Prelle, K. et al. "Establishment of pluripotent cell lines from vertebrate species-present status and future prospects" *Cell Tissues Organs*, 1999, pp. 220-236, vol. 165.

Nandi, A. K. et al. "Regulated expression of genes inserted at the human chromosomal β-globin locus by homologous recombination" *Proc. Natl. Acad. Sci. USA*, 1988, pp. 3845-3849, vol. 85.

Bronson, S. K. et al. "Single-copy transgenic mice with chosen-site integration" *Proc. Natl. Acad. Sci. USA*, 1996, pp. 9067-9072, vol. 93.

Aebischer, P. et al. "Transplantation of neural tissue in polymer capsules" *Brain Research*, 1988, pp. 364-368, vol. 448.

Bell, E. et al. "Living Tissue Formed in vitro and Accepted as Skin-Equivalent Tissue of Full Thickness" *Science*, 1981, pp. 1052-1054, vol. 211, No. 4486.

Cao, Y. et al. "Generation of Neo-Tendon Using Synthetic Polymers Seeded With Tenocytes" *Transplantation Proceedings*, 1994, pp. 3390-3391, vol. 26, No. 6.

Cima, L. G. et al. "Tissue Engineering by Cell Transplantation Using Degradable Polymer Substrates" *Journal of Biomechanical Engineering*, 1991, pp. 143-151, vol. 113.

Kempczinski, R. F. et al. "Endothelial cell seeding of a new PTFE vascular prosthesis" *Journal of Vascular Surgery*, 1985, pp. 424-429, vol. 2, No. 3.

Lanza, R. P. et al. "A Simple and Inexpensive Method for Transplanting Xenogeneic Cells and Tissues Into Rats Using Alginate Gel Spheres" *Transplantation Proceedings*, 1995, p. 3322, vol. 27, No. 6.

Nyberg, S. L. et al. "Evaluation of a Hepatocyte-Entrapment Hollow Fiber Bioreactor: A Potential Bioartificial Liver" *Biotechnology and Bioengineering*, pp. 194-203, vol. 41.

Juttner, C. A. et al. "Early Lympho-Hemopoietic Recovery After Autografting Using Peripheral Blood Stem Cells in Acute Non-Lymphoblastic Leukemia" *Transplantation Proceedings*, 1988, pp. 40-43, vol. 20, No. 1.

Chiu, R. C.-J. et al. "Cellular Cardiomyoplasty: Myocardial Regeneration With Satellite Cell Implantation" *The Society of Thoracic Surgeons*, 1995, pp. 12-18, vol. 60.

Koller, M. R. et al. "Tissue Engineering of Bone Marrow" In: *Tissue Engineering*, 1995, pp. 1728-1744, CRC Press, Inc.

Blaese, R. M. et al. "Treatment of Severe Combined Immunodeficiency Disease (SCID) due to Adenosine Deaminase Deficiency with CD34+ Selected Autologous Peripheral Blood Cells Transduced with a Human ADA Gene" *Human Gene Therapy*, 1993, pp. 521-527, vol. 4, Mary Ann Liebert, Inc, Publishers.

Kim, T. H. et al. "Tissue Engineering of the Liver" In: *Tissue Engineering*, 1995, pp. 1745-1753, CRC Press, Inc.

Freed, L. E. et al. "Tissue Engineering of Cartilage" In: *Tissue Engineering*, 1995, pp. 1788-1806, CRC Press, Inc.

Carlson, B. M. et al. "The regeneration of skeletal muscle fibers following injury: a review" *Medicine and Science in Sports and Exercise*, 1983, pp. 187-198, vol. 15, No. 3.

Brooks, S. V. et al. "Tissue Engineering of Skeletal Muscle" In: *Tissue Engineering*, 1995, pp. 1774-1787, CRC Press, Inc.

Phillips, T. J. et al. "Cultured Epidermal Allografts as Biological Wound Dressings" *Clinical and Experimental Approaches to Dermal and Epidermal Repair: Normal and Chronic Wounds*, 1991, pp. 77-94, Wiley-Liss, Inc.

Mayer, J. E. et al. "Tissue engineering of cardiovascular structures" *Current Opinion in Cardiology*, 1997, pp. 528-532, vol. 12.

Wang, T.-Y. et al. "Multilineal hematopoiesis in a three-dimensional murine long-term bone marrow culture" *Experimental Hematology*, 1995, pp. 26-32, vol. 23.

Golper, T. A. "Continuous Arteriovenous Hemofiltration in Acute Renal Failure" *American Journal of Kidney Diseases*, 1985, pp. 373-386, vol. 6, No. 6.

McCune, J. M. et al. "The SCID-hu Mouse: Murine Model for the Analysis of Human Hematolymphoid Differentiation and Function" *Science*, 1988, pp. 1632-1639, vol. 241.

Seydel, K. B. et al. "Human Intestinal Epithelial Cells Produce Proinflammatory Cytokines in Response to Infection in a SCID Mouse-Human Intestinal Xenograft Model of Amebiasis" *Infection and Immunity*, 1997, pp. 1631-1639, vol. 65, No. 5.

Barr, E. et al. "Systemic Delivery of Recombinant Proteins by Genetically Modified Myoblasts" *Science*, 1991, pp. 1507-1509, vol. 254, No. 5037.

Dhawan, J. et al. "Systemic Delivery of Human Growth Hormone by Injection by Genetically Engineered Myoblasts" *Science*, 1991, pp. 1509-1512, vol. 254, No. 5037.

Culver, K. et al. "Lymphocytes as cellular vehicles for gene therapy in mouse and man" *Proc. Natl. Acad. Sci. USA*, 1991, pp. 3155-3159, vol. 88.

Speiser, D. E. et al. "High Resolution HLA Matching Associated With Decreased Mortality After Unrelated Bone Marrow Transplantation" *Blood*, 1996, pp. 4455-4462, vol. 87, No. 10.

Baxter-Lowe, L. A. et al. "The Predictive Value of HLA-DR Oligotyping for MLC Responses" *Transplantation*, 1993, pp. 1352-1357, vol. 53, No. 6.

Opelz, G. et al. "The Influence of HLA Compatibility on Graft Survival After Heart Transplantation" *The New England Journal of Medicine*, 1994, pp. 816-819, vol. 330, No. 12.

Sheldon, S. et al. "HLA Antigen Mismatching and HLA-Specific Antibodies in Heart Transplantation: Review of a Single Center Experience" *Transplantation Proceedings*, 1992, p. 2438, vol. 24, No. 6.

Yagihashi, A. et al. "HLA Matching Effect in Liver Transplantation" *Transplantation Proceedings*, 1992, pp. 2432-2433, vol. 24, No. 6.

Thorogood, J. et al. "Factors Contributing to Long-Term Kidney Graft Survival in Eurotransplant" *Transplantation*, 1992, pp. 152-158, vol. 54, No. 1.

Opelz, G. et al. "Survival of DNA HLA-DR typed and matched cadaver kidney transplants" *The Lancet*, 1991, pp. 461-463, vol. 338, No. 8765.

McWhinnie, D. L. et al. "The influence of HLA-A,B and -DR matching on leucocyte infiltration in renal allografts" *Tissue Antigens*, 1987, pp. 214-223, vol. 29.

Sada, M. et al. "Importance of HLA-DRB1 Genotyping in Cadaveric Renal Transplantation" *Transplantation Proceedings*, 1992, pp. 2443-2444, vol. 24, No. 6.

Dyer, P.A. et al. "Critical Importance of HLA Antigen Matching in Cadaveric Kidney Transplantation With High Overall Survival Rates" *Transplantation Proceedings*, 1992, p. 2454, vol. 24, No. 6.

Klein, J., In: *Immunology: The Science of Self-Nonself Discrimination*, 1982, pp. 3, 46, 271, 476, John Wiley & Sons.

\* cited by examiner

UNIVERSAL STEM CELLS

CROSS-REFERENCE TO RELATED APPLICATIONS

This application is a continuation of U.S. application Ser. No. 09/047,769, filed Mar. 25, 1998 now abandoned, which claims the benefit of U.S. Provisional application Ser. No. 60/042,358, filed Mar. 25, 1997.

BACKGROUND OF THE INVENTION

The immune systems of mammals have evolved to protect the organism from infectious diseases. Included in the mammalian immune system are many cells that carry out this function by a complex combination of soluble messengers, receptors, adhesion molecules, recognition molecules and signals. Interactions between these components are quite elaborate and take place at specific sites within the organism as well as the primary site of infection. In order to protect the organism from the invasion of viruses, bacteria and other microorganisms, the immune system must be able to distinguish what is self (host) from non-self (invader). The duty is primarily relegated to cell surface molecules known as histocompatibility complex antigens. Each organism has its own set of these molecules to distinguish it from other organisms. In fact, these molecules were discovered when attempts were made to transplant tissues from one host to another.

There are more than thirty of these highly polymorphic molecules that are expressed on the surfaces of virtually all cells. The most important of these molecules are encoded by the major histocompatibility complex (MHC). These genes are categorized as class I, II, or III, depending on their structure, and the role they play in antigen recognition. Class I genes are expressed on virtually all cells, whereas class II gene expression is limited to cells involved in the immune response. It is the class I surface molecules that 'label' the cells as foreign or self. The contribution to transplant rejection made by all other histocompatibility genes is unclear.

MHC is defined as a group of genes coding for molecules that provide the context for the recognition of foreign antigens by T lymphocytes. The MHC is mapped on chromosome 6 in humans and on chromosome 17 in mice (see FIG. 1). The class I are A, B, C in humans and K, D, L in mouse and are highly polymorphic. The class II loci (DP, DQ, DR in humans and I-A, I-E in mouse) are also polymorphic (Klein, 1986). The class III genes, encoding components of the complement system, are between the class I and class II genes. Tissue distribution of class I and class II antigens has clear relevance to transplantation. MHC expression is upregulated in donor organs following allotransplantation and such quantitative changes in expression alter the magnitude of the immune response. Under normal conditions the expression of MHC class I genes is developmentally regulated and is modulated by transcriptional and post-transcriptional mechanisms. MHC antigens are hardly detectable until the midsomite stage of embryogenesis (Drezen et al., 1992). In the adult they are expressed on most somatic cells, but with varying levels in different tissues and cell types, even within a given organ (David-Watine et al., 1990). Expression is highest in lymphoid cells, but undetectable in brain cells, sperm cells at certain stages of differentiation, certain cell populations of the placenta and undifferentiated embryonal carcinoma cells (which exhibit a variety of traits characteristic of the early embryo).

Class II gene expression is limited to specialized antigen presenting cells (APC) of the immune system, which include B lymphocytes, macrophages, tissue resident macrophages and dendritic cells of skin and lymph nodes, but can be induced on activated T cells and in other tissues when stimulated by inflammatory cytokines such as interferon. Class I and class II MHC molecules present antigens to T cells to trigger immune responses to various pathogens (Ellis, 1994). In addition, it has been suggested that these molecules play a significant role in macrophage development (Armstrong et al., 1994).

Structurally, MHC molecules are heterodimers. Class I molecules consist of two noncovalently associated subunits: a polymorphic integral membrane heavy chain of approximately 45 kDa encoded in the MHC locus (see FIG. 2) and a smaller subunit called β-2m, a 12 kDa member of the immunoglobulin superfamily. β-2m is a nonpolymorphic product of a non-MHC-complex-linked gene found on chromosome 15 in humans and on chromosome 2 in mice. The function of β-2m is to stabilize the tertiary structure of the heavy chain. The antigen-binding site is represented by a groove formed between the a1 and a2 domains of the heavy chain, which can accommodate peptides of 8 to 10 amino acids in length. For the class I genes, the HLA-A, -B-, and -C loci encode the heavy chain of the class I molecules. For the class II genes, the products of the A genes of each family (DR, DQ, and DP) combine with the products of the B genes of the same family to make the protein αβ heterodimers that are the class II products. The class II genes are referred to by the suffix A or B, encoding a or β chains, respectively. Class II molecules are formed of 2 polymorphic integral membrane proteins, a (33–35 kDa) and β (28–30 kDa) chains (see FIG. 2) that associate by noncovalent interactions. The antigen-binding site is situated between a1 and β1 domains and it can bind longer peptides.

In reality, HLA expression is extremely complex, for example, class I polymorphism is generated by 64 HLA-A, 132 HLA-B, and 39 HLA-C alleles as shown in Table 1 and mainly due to polymorphic residues in the peptide binding pockets. While only two DRA alleles are known, there have been 149 DRB alleles described (see Table 1). Within the DR gene family, some haplotypes express more than one B gene, but only one expressed A gene and a heterozygous individual may inherit two distinct haplotypes. An additional level of complexity is created by the possibility of the expression of haplotype- and isotype-mismatched αβ dimers, i.e., the assembly of an a chain encoded on one haplotype and the b chain from the second haplotype, or the assembly of two chains encoded by the genes of two different class II loci, e.g., DRa Dqβ.

TABLE 1

Variability of polymorphic genes in the MHC of humans (Newell et al., 1996).

| Gene | Alleles[1] | Residues[2] | Variable residues[3] |
|---|---|---|---|
| HLA-A | 64 | 367 | 110 |
| HLA-B | 132 | 367 | 108 |
| HLA-C | 39 | 367 | 120 |
| DRA | 2 | 229 | 1 |
| DRB | 149 | 237 | 69 |

[1] = number of alleles at that locus
[2] = number of peptide residues in the mature antigen
[3] = number of residues that show some variability In general, only peptides that are derived from autologous proteins and are bound to autologous MHC molecules can be recognized immunologically as 'self'. All other peptides, by definition, are 'non-self', or 'foreign'. This includes peptides derived from autologous proteins that do not bind to autologous MHC molecules, as well as peptides derived from foreign proteins that are bound to autologous MHC molecules. Further complexity is added by the fact that T cells can effectively engage either autologous or allogeneic MHC molecules. In case of a transplant, APC can be derived either from the host or the graft. There are three ways for T cells to recognize alloantigens: 1) allogeneic peptides bound to autologous MHC class II molecules, 2) allogeneic peptides bound to allogeneic MHC class I molecules, and 3) autologous peptides bound to allogeneic MHC class I or II molecules (self peptides not previously seen). Although these proteins may be present in similar tissues of the graft recipient, the specific peptides selected by the allogeneic MHC molecules have never before been encountered by the recipient's immune system, and technically are considered as alloantigens (VanBuskirk et al., 1994). Acute allograft rejection is mediated by cytotoxic T lymphocytes (CTL) upon recognition of 'non-self' antigens bound to MHC class I molecules. T cell activation requires at least two transmembrane signals from T cell surface molecules. One is delivered via the T cell receptor (TcR) complex after productive engagement with MHC class I molecules, another is delivered via at least one of several different adhesion molecules after engagement with their counter-receptor on the tissue cell or APC.

Although the effect of mis-matched MHC can be diminished by immunosuppressive drugs, rejection due to these disparities is still a major barrier to successful organ transplantation. Recombinant DNA technology has made it possible to knock out specific genes in mammals. This technology is predominantly utilized to generate mice lacking in a particular gene. Using these techniques, mice have been created that are missing MHC class I and/or class II antigens. It was hoped that tissues deficient in these molecules would serve as universal donor organs. However, numerous transplantation studies have shown that the absence of these antigens do not make these grafts universally accepted. Furthermore, these MHC-deficient cells cannot perform immune functions to protect the new host from pathogenic invasion.

The goal of transplantation biologists is to successfully replace failing organs or tissues with functional donor organs. However, for transplantation to succeed, two major barriers need to be overcome; first, the availability of suitable donor organs and second, immune rejection. At present, the replacement of failing organs and the treatment of the rejection sequelae is restricted by the limited number of acceptable donors and the need for co-administration of toxic immuno-suppressive drugs in conjunction with long term immuno-suppressive protocols. Current and experimental transplantation protocols rely mainly on sibling donors, other small pools of allogeneic donors, and xenogeneic donors. To overcome these current limitations, there is a growing dependence on tissue matching, non-specific immuno-suppression, and induction of tolerance.

The replacement of the lost function of a diseased organ by transplantation of a healthy organ from a donor to a recipient has been considered a possibility for many years. In practice, this has become clinically feasible only in the last 25 years. Presently, organ transplantation technology is only appropriate in life threatening situations. Two major obstacles have prevented the broad application of transplantation biology. First, the demand for transplantable organs outstrips organ availability, and second, the induction of a vigorous immunologic response results in the rejection of the donor organ (Faustman, 1995). To increase the rate of survival for the transplanted organ, co-administration of toxic immunosuppressive drugs in conjunction with long term immuno-suppressive protocols is common practice. To overcome these limitations, experimental transplantation protocols have been developed.

Although the MHC genes are polymorphic, they are not unique to each individual and it is possible to 'match' the tissue donor to the recipient in such a way as to greatly enhance the probability that a graft will be accepted. This is the principle behind the international bone marrow registry. Tissue typing is usually carried out using serological methods (Bollinger and Sanfilippo, 1989), but DNA analysis is used more and more (Bidwell, 1994). Practically speaking, only the HLA can be matched but even then it would be impossible to match all known HLA in an allogeneic transplant situation. The criteria for determining acceptable mismatches depends on several factors such as the particular organ being transplanted and the mechanism of rejection involved. For these reasons transplantation centers place their emphasis on hierarchy of matching different MHC genes, e.g., HLA-DR>-B>-A, and do not rely solely on the number of mismatches (VanBuskirk et al., 1994). One approach to increase the availability of 'matching' organs might be to develop a bank of stem cells for each MHC type that could be drawn upon for transplantation, similar to that for bone marrow and cord blood stem cells. The major drawbacks to this approach are: the probability of collecting contaminated stem cells; transference of immune cells along with the graft; the expense of collecting cells, educating prospective donors, and maintaining the infrastructure; ethical issues, and availability donors, as exemplified by the problems associated with obtaining bone marrow cells, grafts, and tissues from minority groups. However, the subject invention does not rely on donor availability or ethnic traits. Contamination will be easily controlled and the infrastructure will be substantially less complex.

It is possible to promote graft acceptance by suppressing the host immune system. This is usually done by administering cyclosporin A, azathioprine, or high doses of steroids, however, these drugs are not without side-effects and act in a non-specific manner. Antibodies directed against the T-cell compartment (anti-CD4 and anti-CD8) or the TCR complex (anti-CD3) have also been used to kill or inactivate the recipient T-cells that maybe responsible for graft damage and rejection (Sell et al., 1996a). These antibodies have also been linked to toxic drugs or natural toxins. The nonspecific nature of this type of approach could conceivably disrupt the fine balance between preventing rejection and the innate ability of the immune system to combat disease.

One of the major goals in the field of transplantation is the achievement of long term, drug-free graft acceptance, preferably associated with donor alloantigen-specific immunologic unresponsiveness. This is the operational definition of allogeneic tolerance (VanBuskirk et al., 1994). It is thought that there are both thymic and extrathymic mechanisms of tolerogenesis that can operate in adult mammals. The presentation of peptides by either the donor or recipient MHC molecules is essential in evoking a T-cell response to transplantation antigens (Lechler and Batchelor, 1982, Benichou, et al., 1997). Both direct and indirect allorecognition are involved in the initial T-cell priming to alloantigens expressed on donor passenger leukocytes within recipient lymphoid organs. It is this T-cell recognition of the donor MHC peptides that is responsible for providing help for cytotoxic T lymphocyte activation and the production of donor-directed antibodies by B lymphocytes. Knowledge about the complexity of regulatory mechanisms (direct and indirect allorecognition) that control T-cell responses to donor MHC determinants during graft rejection can be utilized to design peptide based strategies to block graft rejection. Other strategies have included: 1) the use of bone marrow cells as a vehicle for pretransplant delivery of alloantigens to induce tolerance and long term survival of fully allogeneic allografts (Wong, et al., 1996), 2) the intra-thymic injection of alloantigen (Goss et al., 1993), 3) the in vivo treatment of transplant recipients with antibodies to T lymphocytes (Pearson et al., 1992), or MHC antigens in MHC 'masking experiments' (Faustman and Coe, 1991; Faustman, 1995), and to the adhesion molecules such as intercellular adhesion molecule and lymphocyte functional antigen-1 (LFA-1) (Isobe et al., 1992; Faustman, 1995). The induction of tolerance using the monoclonal antibody (BTI-322) in a pre transplant Phase I/II trial as a mechanism to enhance graft survival in renal transplant patients has been shown to reduce graft rejection episodes by 58% compared to conventional triple drug therapy alone.

Other strategies being developed to circumvent transplant rejection and donor shortage include cross-species transplants (xenografts), encapsulation of grafted cells, tissue engineered autologous organs, and the development of genetically engineered 'universal' donor cells.

As of 1996, more than 100,000 people in the US, and another 150,000 internationally have benefited from an organ transplant. Despite the 15% annual increase in demand for transplantable organs, the world supply remains static and in some countries is on the decline. One possible solution to alleviate the problem of donor shortage is xenotransplantation, i.e., transplantation of organs from animals to humans. The key issues for successful xenotransplantation are: managing the risk of zoonoses; compatibility of donor organ in size, anatomy, and physiology; overcoming immune rejection of the graft; and the ethical issues (Auchincloss, 1988; Faustman, 1995 and Regalado, 1996). The major problem with animal organs for transplantation goes beyond the compatibility of MHC antigens and introduces another level that deals with the recognition of species-specific antigens. These differences in antigens are responsible for the hyperacute rejection (HAR) phenomenon that can occur within minutes following transplant surgery. A number of studies have centered on introducing the human genes encoding complement inhibitory proteins such as the membrane co-factor protein and decay accelerating factor (CD59) into pigs. Sykes et al., (1991) proposed that the use of xenograft bone marrow transplantation may provide another therapeutic approach to induce hyporeactivity towards a xenogeneic organ donor, while maintaining normal immune function. This approach to tolerize recipients is not feasible for use in human transplantation, primarily due to the high risk associated with myeloablative conditioning regimens required to achieve re-engraftment of allogeneic bone marrow (Sykes et al., 1991).

The science of tissue engineering combines techniques involved in transplantation, cell culture, biomaterials, and genetic engineering. Tissue engineered products include bio-material-based scaffolding for the growth of tissues, implantation of isolated cells, administration of biologically active compounds to effect endogenous tissue and combinations of biomaterials and active compounds. There are a number of studies involving cartilage and bone repair, periodontal repair and peripheral-nerve regeneration, glottic insufficiency, urinary incontinence, post-operative adhesion, metabolic diseases involving liver bioreactors, insulin-dependent diabetes, chronic pain, and neurological diseases and skin repair. The need for autologous tissue will limit the number of centers able to perform these types of services and may make wide-scale use of these therapies impractical.

The primary goal in encapsulation as a cell therapy is to protect allogeneic and xenogeneic cell transplants from destruction by the host immune response. If successful, this approach will eliminate the need for immuno-suppressive drug therapy. Furthermore, the encapsulation will also protect the host from the transplanted cell (potential for dividing cells to cause tumors). Bioencapsulation technologies have shown promise for the encapsulation and transplant of cell populations such as pancreatic islet cells (Siebers et al., 1990; Lanza and Soon-Shiong, 1991) and liver hepatocytes (Chang, 1995; Stange and Mitzner, 1996). This technological approach has been considered for the treatment of hemophilia B, diabetes, chronic pain, and Alzheimer's Disease. The encapsulation of genetically altered cells may offer many advantages over autologous ex vivo gene therapy including their use with 'universal cells' containing the desired gene and immunoisolated through encapsulation.

The much touted goal of organ transplantation is to generate 'generic' or universally-compatible tissues. In the hunt for this 'holy grail' of transplantation, others have attempted to create such a cell by eliminating the expression of class I molecules (U.S. Pat. Nos. 5,574,205; 5,416,260; 5,413,923; and PCT/US90/04178). The development of transgenic mice have made it possible to examine the effect of eliminating class I antigens by creating a 'knock out' for the β-2 microglobulin (β-2m) gene. It is well accepted that the function of the β-2m is to stabilize the tertiary structure of the heavy chain of MHC class I and that the absence of the β-2m, from the MHC class I complex adversely affects the transport of the molecule (heavy chain) to the cell surface by the endoplasmic reticulum. This approach to transplantation has not been successful for it appears that cells lacking MHC antigens are targets for natural killer (NK)-mediated cytolysis and are therefore still vulnerable to immune rejection. This argument was further supported by studies demonstrating that rejection could be prevented if NK cells were depleted from the recipient by pretreatment with anti-NK1.1 antibodies. Other published data on NK function indicate that NK cells will kill target cells that have lost or have altered expression of self-MHC antigens: 'missing self hypothesis' (Karre et al., 1986 and Carlow et al., 1990). The role of the 'missing self' hypothesis in NK-mediated cytolysis is still controversial. Kim et al., (1994) showed that MHC class I surface expression does not influence NK-mediated cytolysis of a target cell and Markmann et al., (1994) found little indication that grafts of non-hematopoietic tissue lacking the expression of MHC class I would be rejected by NK cells.

The theory that tissues devoid of MHC expression could be used as universal donor tissues for transplantation has turned out not to be the panacea for the rejection phenomena. Not only are MHC-deficient cells rejected by the immune system, they are unable to present self and non-self antigens to immune surveillance, seriously undermining the ability of the immune system to recognize the presence of pathogenic organisms. Tissues generated according to the methods of the subject invention have the advantage of being able to overcome immune rejection, both by matching HLA and circumventing NK-mediated cytolysis, without jeopardizing their ability to present antigens in the context of class I and/or class II MHC. No other technology can accomplish all of these things simultaneously.

Two important technologies have recently been developed: the isolation of embryonic stem (ES) cells as permanent in vitro cell lines that can repopulate the blastocyst stage embryo (Evans and Kaufman, 1981) and contribute to the germ-line tissue (Bradley et al., 1984), and the discovery that mammalian cells can recombine introduced vector DNA with a homologous chromosomal target, a process known as gene targeting (Smithies et al., 1985; Thomas and Capecchi, 1987). Gene targeting in ES cells by homologous recombination allows introduction of exogenous DNA sequences into virtually any gene of the germ line so that the gene function can be studied by mutational analysis in vivo. The factors that increase the efficiency of homologous recombination are: a syngeneic background (targeting or homology cassettes derived from the cell to be targeted) (Te Riele et al., 1992), the length of homology between the targeting vector and the genomic DNA of the targeted cell, and the cell's position in the cell cycle (recombination peaks in early S phase) (Capecchi, 1994).

The underlying concept of generating transgenic organisms by homologous recombination is relatively simple: a targeting vector carrying a positive selectable marker flanked by sequences homologous to the genomic target gene is constructed and introduced by transfection into an ES cell line. The homologous flanking sequences enable targeted insertion into the genome and the selectable marker replaces the original wild-type sequence. Subsequently, the successfully targeted ES cell line is injected into blastocysts (3.5 day embryos; 32 cell stage) or co-cultured with morulae (2.5 day embryos; 8–16 cell stage) and contributes to the tissues of the developing animal including the germ line. Breeding will produce homozygous animals exhibiting the phenotype of the inserted mutation in all cells (Galli-Taliadoros et al., 1995).

Although mammalian cells can mediate recombination between homologous DNA sequences very efficiently, they have an even greater predilection for mediating nonhomologous recombination. Recombination occurs via the homologous sequences located within the targeting construct, and does not integrate sequences outside the homology cassette. In contrast, random integration occurs via the ends of the targeting construct, and leads to integration of the entire construct, often in head to tail multimers. Inclusion of a negative selection suicide gene outside the region of homology, therefore allows selection against cells that have undergone non-homologous recombination. Correctly targeted cells will be unaffected by negative selection. The problem is to identify homologous recombination events among the vast pool of nonhomologous recombination events. The invention of methods that lower the background of these nontargeted events and improve screening techniques, namely, positive-negative selection (Mansour et al., 1988), promoterless resistance markers (Schwartzberg et al., 1989), use of polymerase chain reaction (PCR) in screening of pools of clones (Joyner et al., 1989), and polyadenylation (polyA) signal-less markers which produce stable transcripts only if inserted upstream of a genomic polyA signal (Joyner et al., 1989), have made targeted mutations at many nonselectable loci easier to detect.

As can be understood from the above, there remains a need in the art for a means to prepare cells and tissues in which the expression of histocompatibility antigens can be selected for and controlled in order to utilize these cells and tissues in transplantation and other applications.

BRIEF SUMMARY OF THE INVENTION

The subject invention concerns materials and methods for preparing cells having a pre-selected expression of MHC antigens. Typically, these cells are multi-potential stem cells. Cells of the subject invention can be used to generate histocompatible tissues/organs for transplantation. The process of the subject invention comprises the use of targeting vectors capable of gene knockout, insertion of site-specific recombination sequences, and the replacement of histocompatibility alleles in the stem cell. In one embodiment, the MHC of mammalian stem cells are altered in a stepwise fashion. Novel knockout vectors are used to delete designated regions of one chromosome. Recombination cassette vectors are then used to delete the same region on the second chromosome and deposit a site-specific recombination cassette which can be utilized by the replacement vectors containing a pre-selected gene in order to produce a genetically engineered cell having a new, pre-selected haplotype.

The subject invention also concerns the novel vectors used to prepare cells of the invention. Encompassed within the scope of the invention are knockout vectors, recombination cassette vectors, and replacement vectors for use in human and mammalian cells.

The subject invention also concerns cells, both human and mammalian, genetically engineered according to the methods of the present invention. The cells can be embryonic, mesenchymal, mesodermal or tissue-specific stem cells. These cells are engineered to accept new MHC genes because of the incorporation of site-specific recombination sequences strategically placed in the MHC locus of the subject cell. These 'immunologically camouflaged' cells and tissues of the present invention can be used to prepare extensive stem cell banks comprised of "matched" cells for transplantation cell/tissue banks.

The subject invention also concerns transgenic non-human mammals expressing pre-selected histocompatibility genes. Transgenic mammals can be produced from cells genetically engineered using materials and methods of the present invention.

DETAILED DESCRIPTION OF THE INVENTION

Figure 1:
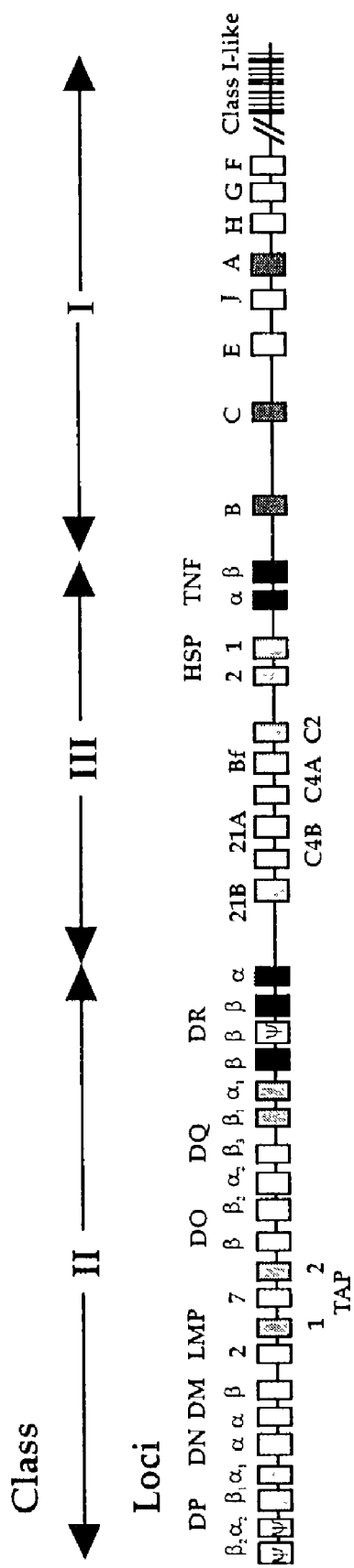
FIG. 1 shows a schematic diagram of human MHC genes.

The subject invention concerns materials and methods for preparing cells expressing a pre-selected or heterologous histocompatibility gene or allele. Typically, these cells are multi-potential stem cells. Cells of the subject invention can be used to generate compatible tissues/organs for transplantation. One embodiment of the process of the subject invention comprises the use of targeting vectors capable of gene knockout, insertion of site-specific recombination cassettes, and the replacement of histocompatibility alleles. As used herein, the term "pre-selected" means that the chosen gene or allele to be integrated into a chromosome of the cell is one that is not normally expressed by the unaltered cell.

The subject invention also concerns novel vectors used to prepare cells of the invention. Encompassed within the scope of the invention are knockout vectors, recombination cassette vectors, and replacement vectors for use in human and mammalian cells. Specifically exemplified are vectors suitable for use human cells. These include Knockout vectors: pHKO-B/C and pHKO-DR Recombination Cassette vectors: pHRC-B/C and pHRC-DR Replacement vectors: pHRE-B(44) and pHRE-DR(7)

The construction of these vectors is described in more detail herein.

The subject invention also concerns cells genetically engineered according to the methods of the present invention. Contemplated within the scope of the invention are both human and mammalian cells. Mammalian stem cells that can be used with the present invention include, for example, primate (Thomson and Marshall, 1998; Thomson et al., 1996; Thomson et al., 1995), pig (Shim et al., 1997; Wheeler, 1994), mouse, rat, sheep and cow cells. The cells can be embryonic, mesenchymal, mesodermal or tissue-specific stem cells. Cells contemplated within the scope of the present invention include those stem cells in which normal histocompatibility gene expression has been altered. Examples of altered stem cells are shown in Table 4. In a preferred embodiment, the stem cells are human stem cells that have been engineered to be positive for HLA-A, negative for HLA-B, negative for HLA-C, and negative for HLA-DRB(1–9). Specifically exemplified are cells that are genotypically homozygous for the HLA-A2 allele (i.e., cells that are HLA-A2, -B$^-$, -C$^-$, -DR$^-$; see Table 4, No. 6) Universal stem cells of the invention, such as those that are HLA-A2, -B$^-$, -C$^-$, -DR$^-$, are capable of accepting new HLA-B and HLA-DR genes selected to match the desired HLA alleles. These cells can accept the new HLA genes because of the incorporation of site-specific recombination sequences (SSRS) strategically placed in the HLA locus of the subject cell. These 'immunologically camouflaged' cells and tissues of the present invention can be used to prepare extensive stem cell banks comprised of "matched" cells for transplantation cell/tissue banks.

The subject invention also concerns transgenic non-human mammals that express pre-selected histocompatibility genes that can be produced from cells genetically engineered using materials and methods of the present invention. In a preferred embodiment, the transgenic animals express human histocompatibility genes on their tissues and organs. The mammals can include, for example, primates, pigs, sheep and cows. Sequences of porcine MHC have been described (Peelman et al., 1996, Velten et al., 1998, and Sullivan et al., 1997) methods for preparing transgenic animals are well known in the art.

One embodiment of a method for producing a cell expressing at least one pre-selected histocompatibility gene, comprises the steps of deleting a designated region of histocompatibility gene complex on a first chromosome of the cell; deleting the designated region of histocompatibility gene complex on a second chromosome of the cell; and replacing the deleted region of histocompatibility gene complex of the cell with a pre-selected histocompatibility gene. More preferably, the pre-selected histocompatibility gene is a major histocompatibility gene. Most preferably, the major histocompatibility gene is a human gene.

In a preferred embodiment of the invention, the method for producing a cell expressing at least one pre-selected histocompatibility gene, comprises the steps of:

a) deleting a designated region of a histocompatibility gene complex on a first chromosome of the cell by transforming the cell with a knockout vector comprising a selectable marker and two homology cassettes capable of deleting the designated region of a histocompatibility gene complex by homologous recombination;

b) deleting the designated region of histocompatibility gene complex on a second chromosome of the cell and inserting a site-specific recombination cassette on the chromosome by transforming the cell after step (a) with a recombination cassette vector comprising a selectable marker, two homology cassettes capable of deleting the designated region of a histocompatibility gene complex by homologous recombination and a site-specific recombination cassette; and c) replacing the deleted region of a histocompatibility gene complex of the cell by transforming the cell after step (b) with a replacement vector comprising a pre-selected histocompatibility gene that can be expressed in the cell.

In one embodiment of the methods of the invention, the selectable marker is a positive selectable marker gene, a negative selectable marker gene or both. Positive selection marker genes that can be used with the methods and vectors of the subject invention include green fluorescent protein (gfb), β-galactosidase (β-gal), blasticidin deaminase (bsd), dihydrofolate reductase (dhfr) and neomycin (neo). Negative selection marker genes that can be used with the methods and vectors of the subject invention include diptheria toxin-A (DT-A) and thymidine kinase (TK). Other suitable positive and negative selection marker genes are known in the art and can be used according to the present invention.

Site-specific recombination cassettes that can be used with the methods and vectors of the subject invention can include, for example, the bacteriophage P1 Cre/loxP system, and heterospecific variants thereof (Sauer, 1996), and the yeast FLP-FRT system. Other suitable site-specific recombination cassette systems known in the art can also be used.

The subject invention also concerns methods for producing cells and tissue that express at least one heterologous histocompatibility gene and at least one therapeutic gene. Therapeutic genes include those genes that when expressed confers a therapeutic effect or benefit to a person receiving the cell or tissue. Conditions which can be treated by this method include malignancy, autoimmune diseases, genetic defects and tissue rejection. In one embodiment, the therapeutic gene is carried on a replacement vector. When the cells are transformed with the replacement vectors, the therapeutic gene(s) and histocompatibility gene(s) are inserted into a deleted region of the host chromosome. In one embodiment, a histocompatibility gene is operably linked with a therapeutic gene. Therapeutic genes can include, for example, genes that encode cytokines, immunosupressive proteins, and the like. Therapeutic genes can also be genes that correctly encode or express a protein that is defective or incorrectly expressed in the recipient organism. Therapeutic genes also include polynucleotide sequences that encode RNA that is antisense to RNA which requires down regulation for therapy. The regulation of therapeutic gene expression can be linked or independent of heterologous histocompatibility gene expression.

The cells and tissues of the subject invention can be used in tissue transplantation to treat tissue or organ disfunction of a recipient animal caused by genetic defects, infectious diseases, trauma, malignancy, autoimmune disease, drug abuse and the like.

Cells and tissue of the inventions expressing at least one heterologous histocompatibility gene can be used to provide compatible cells and tissue for tissue transplants, bone marrow transplants, reconstructive/cosmetic surgery, and to treat genetic diseases and provide genetic therapy.

The solutions provided in this invention include: 1) optimizing the regions of homology in the knockout and site-specific recombination vectors which will promote efficient homologous recombination; 2) incorporating efficient selectable markers which allow rapid and reliable selection of correctly targeted cells; 3) optimizing the frequency with which DNA can be introduced into normal cells, increasing the probability of homologous recombination events; 4) designing a selection strategy that is not heavily dependent on drug selection which thus facilitating the maintenance of functional targeted cells; 5) exploiting FACS to identify, sort and collect as single cell depositions such rare events as correctly targeted cells; 6) attempting simultaneous multiple knockouts to minimize the number of genetic manipulations, selections, and expansions; 7) using proprietary stem cell growth factors capable of maintaining the primitive nature of stem cells; 8) using stem cells, which maintain multipotential function through repeated passage and are non-quiescent, a feature that will promote homologous recombination; 9) designing a knockout/replacement strategy that will limit the number of manipulations necessary; and 10) designing a knockout strategy for deleting a specific allele on both chromosomes. The direct benefit to patients will be through increased availability of transplantable tissues, a higher probability of transplant success, increased indications for transplantation, and reduced cost for transplants and supportive care.

The strategy set forth in this invention is founded on four conclusions: 1) It is not only impossible in a practical sense, but unnecessary to match all the HLA molecules between the graft and the recipient. This is based on the tremendous polymorphism of the HLA alleles (see Table 1) and observations that for human liver transplants, HLA-A and HLA-B matching significantly improves graft survival, but HLA-DR has minimal effect; in heart transplants there is no correlation between graft survival and HLA-A and HLA-B matching, but HLA-DR matches reduces the number and severity of rejection episodes; and for kidney grafts a HLA-DR match is required, but only 1 HLA-A or HLA-B match is necessary (Sell et al., 1996b).; 2) It is not possible to facilitate transplant acceptance by eliminating class I antigens entirely. Other mechanisms involving 'missing self' that promote rejection have been discussed earlier in this proposal.; 3) To eliminate MHC antigens completely would place the recipient in danger of immunological incompetence. The MHC provides a means of communicating within the immune system, a breakdown in MHC/peptide/TcR cooperation would leave 'holes' in the immune response. In case of class I antigens, the grafted tissue will be unable to alert the immune system to the presence of an invading virus and in the case of a marrow graft, the APC and T lymphocytes, which require class II for antigen presentation, would not be capable of protecting the host, seriously undermining the ability of the transplanted immune system to recognize a number of harmful invaders.; and 4) A complete repertoire of HLA molecules is unnecessary for survival. This is based on the observations that some individuals express only two DRB alleles and the reports of a healthy adult expressing no HLA-A (Ishikawa, et al., 1995). Based on these conclusions, it should be possible to reduce the number of mismatched MHC molecules without invoking either NK-mediated cytolysis or other 'missing self' rejection mechanisms. The exact number and choice of these genes must be empirically determined and will most likely vary for different tissue types. It should also be possible to supplant one or more of these genes by one that will 'match' the recipient. This should help cover any 'holes' in the immune response created by the knockouts.

Despite the number of polymorphic alleles that have been described, their distribution in the general population is disproportionate. By noting the allele frequencies of HLA-A, -B, and -DR for different ethnic groups, it is possible to suggest an approach that will cover a reasonable section of the population. Two HLA-A alleles are present in approximately 45% of the Western world. HLA-A2 is present on average in 25% in most populations (see Tables 2&3). The ubiquitous nature of HLA-A2, and in particular the A*0201 allele, suggests that it is important in protective immunity. For example, there are four possible approaches to dealing with HLA-A; 1) obtain A/A null stem cells, 2) perform 2 HLA-A knockouts to create A/A null stem cells, 3) perform 1 HLA-A knockout and one replacement, or 4) allow the stem cell to determine the specificity of the allele. It seems reasonable to suggest that stem cells are obtained from an individual with the HLA-A2 haplotype. This will eliminate any genetic manipulation of HLA-A and produce a cell that will be compatible with a significant number of possible recipients. Therefore, the prototype stem cell of the invention is homozygous for HLA-A2. The relevance of HLA-C in transplant rejection is debatable, therefore, in one embodiment of the invention, the HLA-C is simultaneously deleted along with HLA-B and all the alleles of HLA-DRB, but is not replaced. The resulting HLA-A2, -B$^-$, C$^-$, DR$^-$ (see Table 4, row 6) stem cell population is capable of accepting new HLA-B and HLA-DR genes of choice due to the incorporation of site-specific recombination sequences strategically placed in the HLA locus and can be used as a progenitor line for the creation of an entire bank of haplotype-specific stem cells.

TABLE 2

Haplotype frequencies and linkage disequilibriums within HLA-A, -B, -DR loci in selected populations. (Dyer and Middleton, 1993; Spencer Wells R. and Parham P. (1996))

| Ethnic Group | Haplotype HLA- | | | HF (%) | LD |
|---|---|---|---|---|---|
| | A | B | DR | | |
| USA | 1 | 8 | 3 | 6.4 | 6.4 |
| | 3 | 7 | 2 | 2.6 | 2.6 |
| | 2 | 7 | 2 | 1.3 | 1.3 |
| | 3 | 35 | 1 | 1.3 | 1.3 |
| | 3 | 7 | 15 | 1.0 | 1.0 |
| | 29 | 44 | 7 | 1.1 | 1.1 |

TABLE 2-continued

Haplotype frequencies and linkage disequilibriums within HLA-A, -B, -DR loci in selected populations. (Dyer and Middleton, 1993; Spencer Wells R. and Parham P. (1996))

| Ethnic Group | Haplotype HLA- A | B | DR | HF (%) | LD |
|---|---|---|---|---|---|
| Australian | 1 | 8 | 3 | 7.6 | 7.6 |
| | 1 | 7 | 15 | 3.4 | 3.4 |
| | 2 | 7 | 15 | 2.5 | 2.5 |
| British | 1 | 8 | 3 | 6.2 | 6.2 |
| | 1 | 35 | 1 | 2.2 | 2.2 |
| Canadian | 1 | 8 | 3 | 5.2 | 5.1 |
| | 3 | 7 | 15 | 4.3 | 4.3 |
| | 2 | 7 | 15 | 1.4 | 1.3 |
| French | 1 | 8 | 3 | 3.9 | 3.9 |
| | 29 | 44 | 7 | 2.2 | 2.2 |
| | 3 | 7 | 15 | 1.8 | 1.8 |
| German | 1 | 8 | 3 | 5.8 | 5.8 |
| | 3 | 7 | 15 | 2.5 | 2.5 |
| | 2 | 8 | 3 | 1.2 | 1.2 |
| Japanese | 24 | 52 | 15 | 8.3 | 8.3 |
| | 33 | 44 | 13 | 4.9 | 4.9 |
| | 24 | 7 | 1 | 3.6 | 3.6 |
| Taiwanese | 24 | 39 | 12 | 10.4 | 10.0 |
| | 2 | 48 | BL | 6.1 | 6.1 |
| | 24 | 60 | 14 | 4.1 | 3.8 |

TABLE 3

HLA-A, -B, -DR allele frequencies in different ethnic groups. (Dyer and Middleton, 1993)

| Ethnic Group | HLA Allele (%) A | B | DR |
|---|---|---|---|
| USA | 2 (28.3) | 44 (10.4) | 7 (15.1) |
| | 1 (16.9) | 7 (10.0) | 4 (12.8) |
| | | 8 (10.0) | 13 (12.7) |
| | | | 15 (10.8) |
| | | | 3 (10.1) |
| | | | 1 (10.1) |
| Total Australian | (45.2) | (30.4) | (71.6) |
| | 2 (26.3) | 44 (15.6) | 4 (22.5) |
| | 1 (16.9) | 8 (12.8) | 15 (14.9) |
| | | 7 (10.3) | 1 (11.4) |
| | | | 3 (9.6) |
| | | | 7 (7.4) |
| Total British | (43.2) | (38.7) | (65.8) |
| | 2 (24.1) | 8 (13.7) | 7 (20.8) |
| | 1 (15.0) | 44 (10.3) | 4 (13.9) |
| | | 35 (8.5) | 3 (12.4) |
| | | | 1 (10.7) |
| | | | 15 (10.2) |
| Total Canadian | (39.1) | (32.5) | (68.0) |
| | 2 (26.7) | 44 (13.3) | 4 (18.2) |
| | 1 (18.6) | 7 (11.1) | 7 (14.4) |
| | | 8 (11.1) | 15 (14.4) |
| | | | 1 (12.0) |
| | | | 3 (11.3) |
| Total French | (45.3) | (35.5) | (70.3) |
| | 2 (21.3) | 44 (10.8) | 7 (13.5) |
| | 1 (13.7) | 35 (8.4) | 13 (13.2) |
| | | 7 (7.5) | 15 (11.2) |
| | | | 3 (11.0) |
| | | | 1 (10.8) |
| | | | 4 (10.8) |
| Total German | (35.0) | (26.7) | (70.5) |
| | 2 (27.8) | 7 (10.7) | 11 (18.1) |
| | 1 (18.0) | 8 (9.8) | 4 (13.4) |
| | | 44 (9.2) | 7 (11.3) |
| | | | 13 (10.3) |
| | | | 3 (10.1) |
| | | | 1 (9.5) |
| Total Japanese | (45.8) | (29.7) | (72.7) |
| | 24 (35.1) | 52 (10.7) | 4 (22.8) |
| | 2 (24.4) | 60 (10.7) | 15 (17.4) |
| | | 44 (7.4) | 8 (13.3) |
| | | | 9 (13.0) |
| | | | 3 (7.8) |
| Total Taiwanese | (59.5) | (28.8) | (74.3) |
| | 24 (61.0) | 60 (32.3) | 12 (23.6) |
| | 2 (18.1) | 39 (15.8) | 11 (19.3) |
| | | 48 (14.5) | BL (12.4) |
| | | | 14 (12.2) |
| | | | 4 (8.7) |
| Total | (79.1) | (62.6) | (76.2) |

Using a universal human stem cell of the subject invention, producing cells having a new haplotype would involve a single step, thus making the establishment of a representative stem cell bank relatively easy. Contemplated within the scope of the present invention are cells comprising at least one heterologous human histocompatibility gene from any of the alleles of these human genes (Dyer and Middleton, 1993). Thus, a cell of the invention could be prepared to express any HLA-A allele, HLA-B allele, HLA-C allele, HLA-DR allele, HLA-DQ allele and HLA-DP allele.

It is hypothesized that it would not be necessary to match all of the heterozygous alleles of HLA-B, C, and the multiple DRB, but it would be sufficient to provide a single matching class I and/or II allele. In order to match the majority of recipients, the number of replacements necessary would be relatively small. Approximately 30% of people of Western origin could accept a transplant exhibiting one of three alleles of HLA-B and 70% by six alleles of DR. In the same vein, HLA alleles are inherited as supermotifs and supertypes (Sidney, et al., 1996; Browning and Krausa, 1996) or en bloc haplotypes represented at significantly higher frequencies than would be predicted. For example, HLA-A1, B8, DR3 is found in 10% of Caucasians. Tissues arising from stem cells bearing this haplotype would be successfully transplanted into a high percentage of recipients. The development of transplantable tissues for minority ethnic groups would be as simple. For the prototypic cell example, vectors inserting HLA-B44 and HLA-DR7 into a stem cell will be generated.

Figure 2:
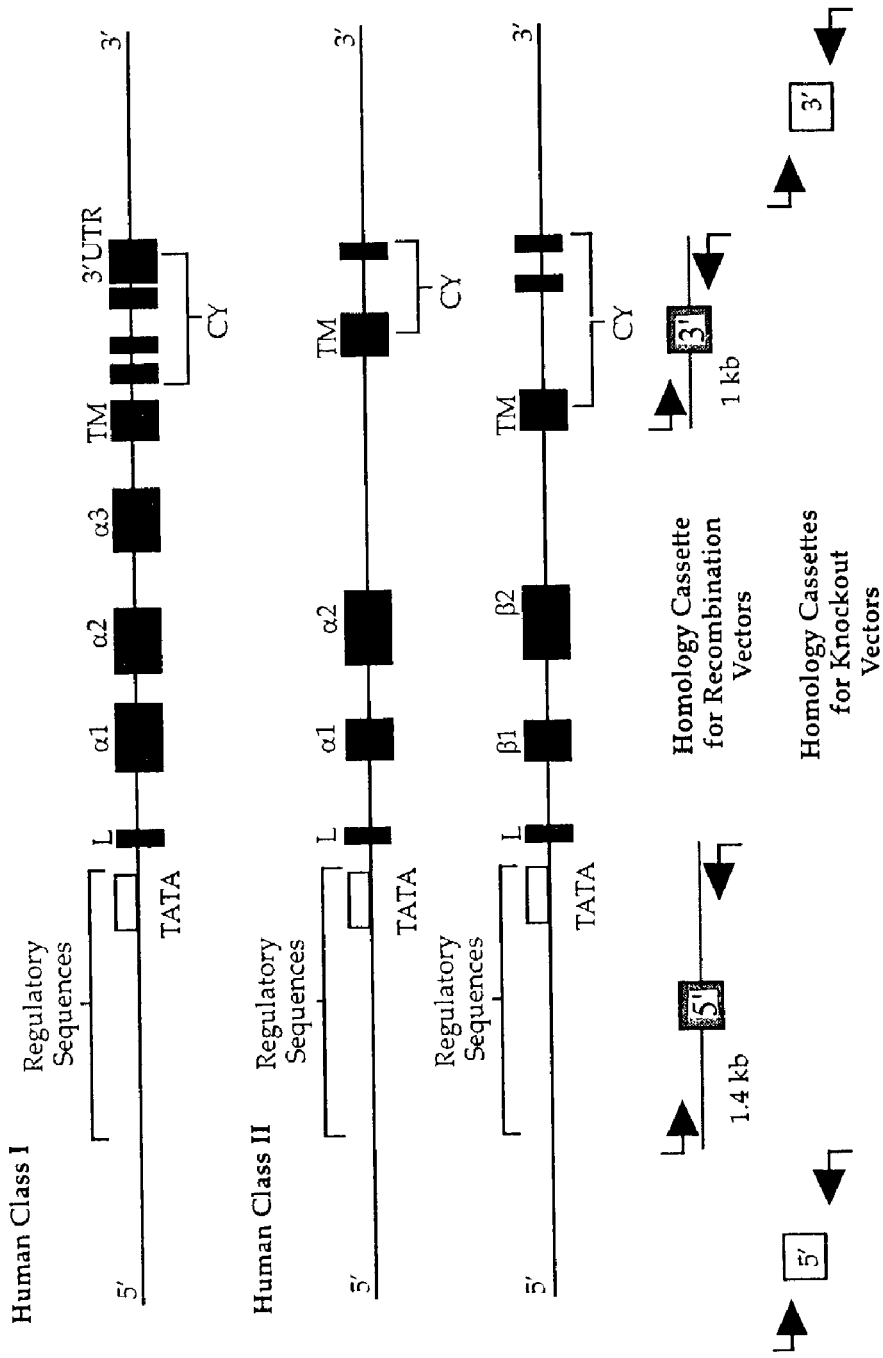
FIG. 2 shows a schematic diagram of human class I and class II MHC genes, as well as the location of homology cassettes for knockout vectors and recombination vectors. Arrows indicate primers for the amplification of these regions from chromosomal DNA.
Figure 3:
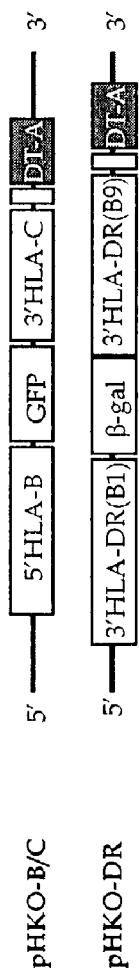
FIG. 3 shows a schematic diagram of prototype genetic vectors required to alter MHC expression.
Figure 3:
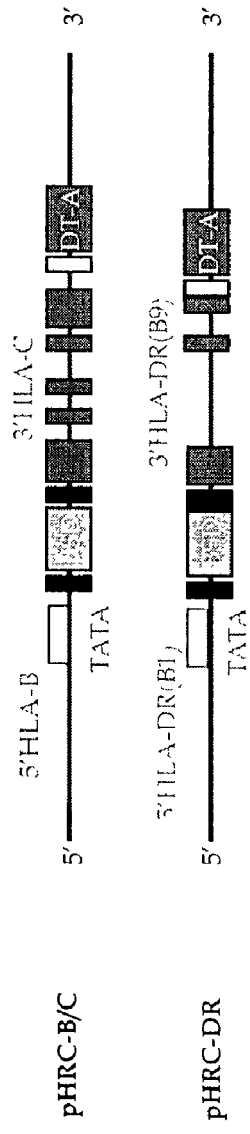
Figure 3:
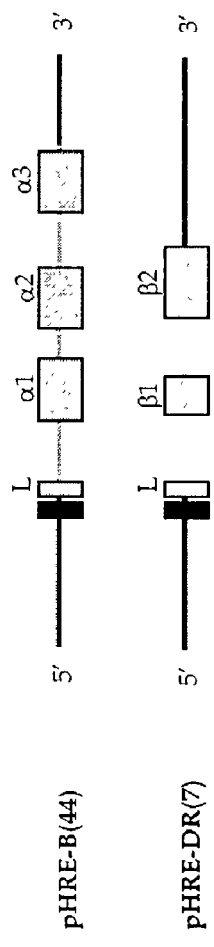
Figure 4:
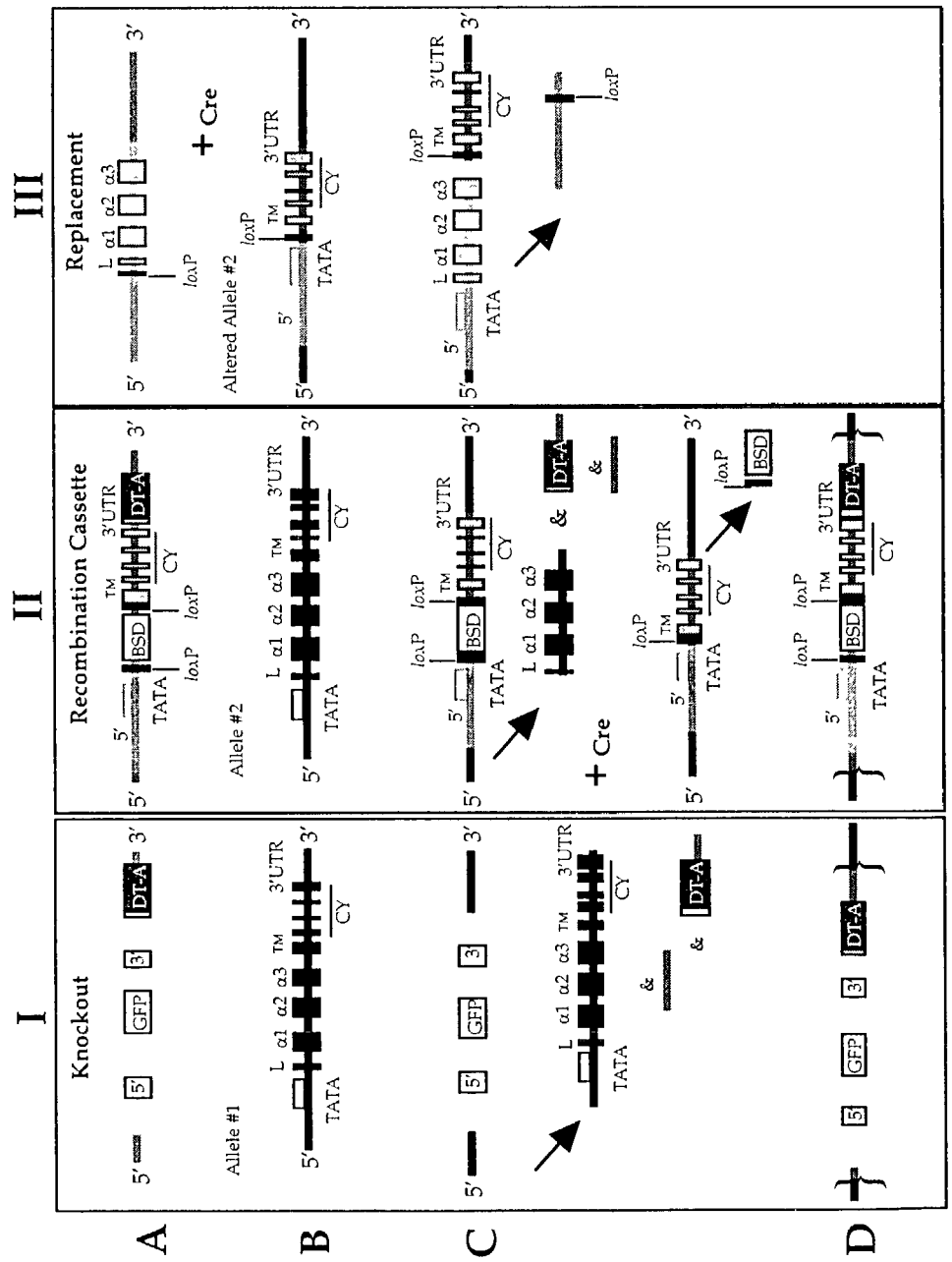
FIG. 4 shows three phases of the method for producing a cell having a pre-selected histocompatibility gene: Phase I Knockout vectors, Phase II Recombination vectors, and Phase III Replacement vectors.

In one embodiment, methods of the subject invention comprise a three stage genetic engineering process involving vectors capable of gene knockout, insertion of site-specific recombination cassettes, and replacement of HLA alleles (see FIG. 3). The knockout vectors are used to delete the designated regions of one chromosome (see FIG. 2). The recombination cassette vectors are used to delete the same region on the second chromosome and deposit a site-specific recombination cassette which can be utilized by the replacement vectors in determining the new haplotype (see FIG. 4). Given its wide applicability, different classes of stem cells could be used in conjunction with the subject invention. Embryonic stem cells are an ideal cell to manipulate because of the number of tissues that can be generated. Alternatively, tissue-specific stem cells, i.e., hepatocytes, hematopoietic stem cells, and β-islet cells, could also be targeted. Mesenchymal stem cells are easily obtained and will maintain multipotentiality through the repeated in vitro passaging necessary to achieve high cell concentrations for multiple genetic manipulations. The conditions required for their growth and differentiation are well described (Caplan and Bruder, 1997) and many of the tissues currently transplanted, i.e., bone, cartilage, tendon, ligament, muscle, connective tissue, and marrow stroma, are of mesenchymal origin.

The subject invention utilizes three types of genetic constructs: Phase I knockout vectors, Phase II recombination vectors, and Phase III replacement vectors in order to alter the histocompatibility phenotype of the target cell. Plasmid constructs containing the selectable markers under the control of appropriate promoters have already been completed as has the bsd/loxP cassette. The remaining components will be assembled using current molecular techniques which are discussed herein. FIG. 3 is a schematic diagramming the components, structure, and organization of all the vectors of the subject invention.

Figure 5:
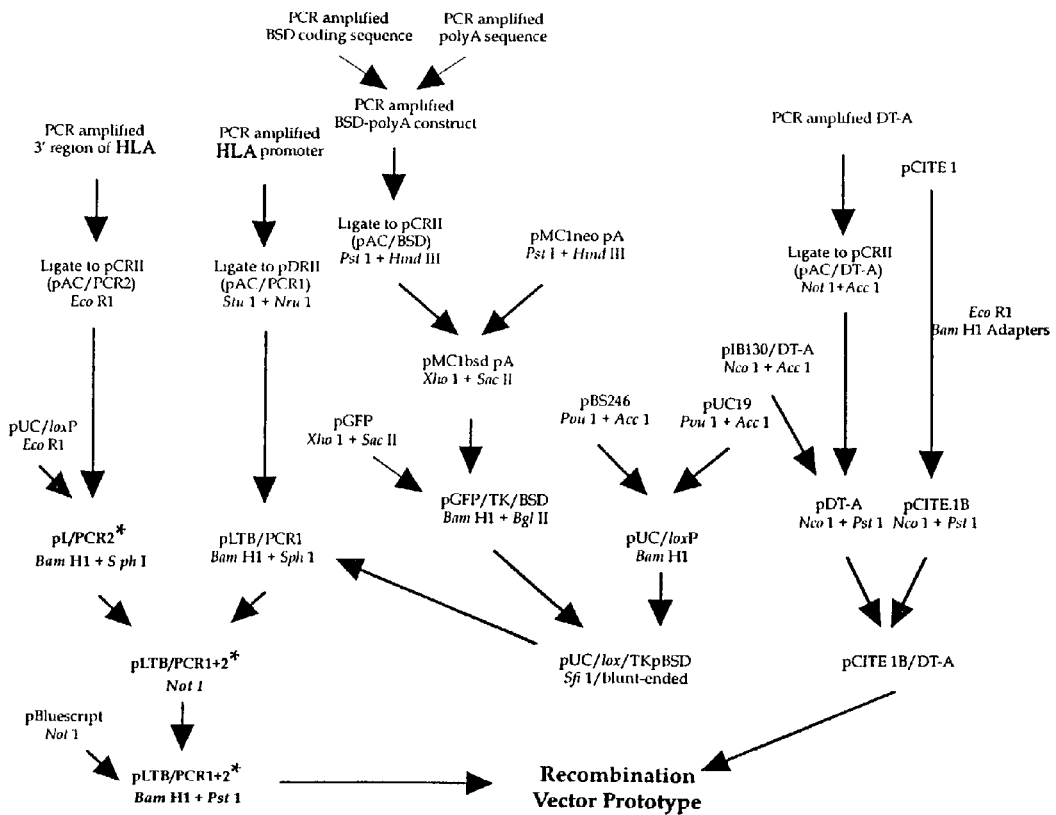
FIG. 5 shows steps for construction of a prototypical recombination vector. PCR1 and PCR2 are any of the homology regions for any of the genes to be deleted or replaced.
Figure 5:
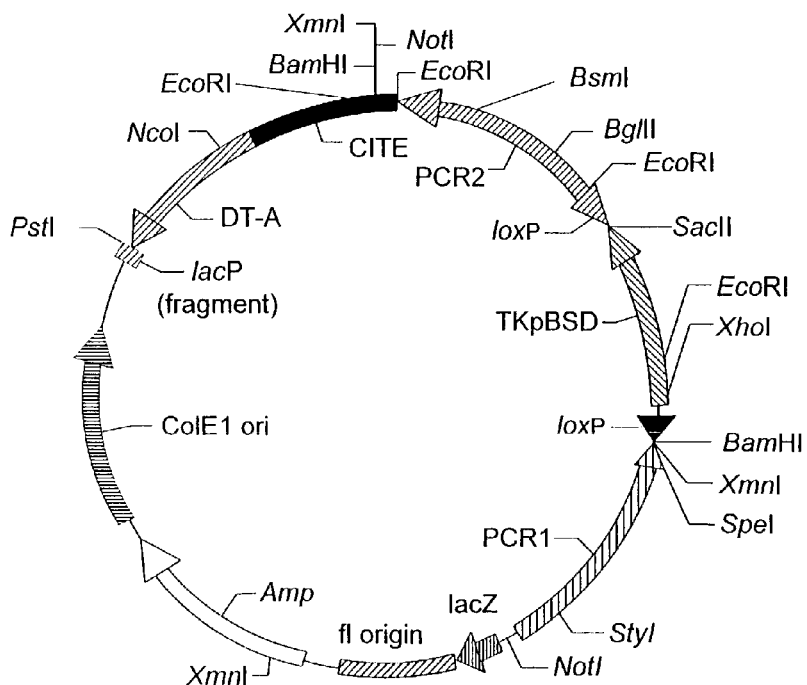
Figure 6:
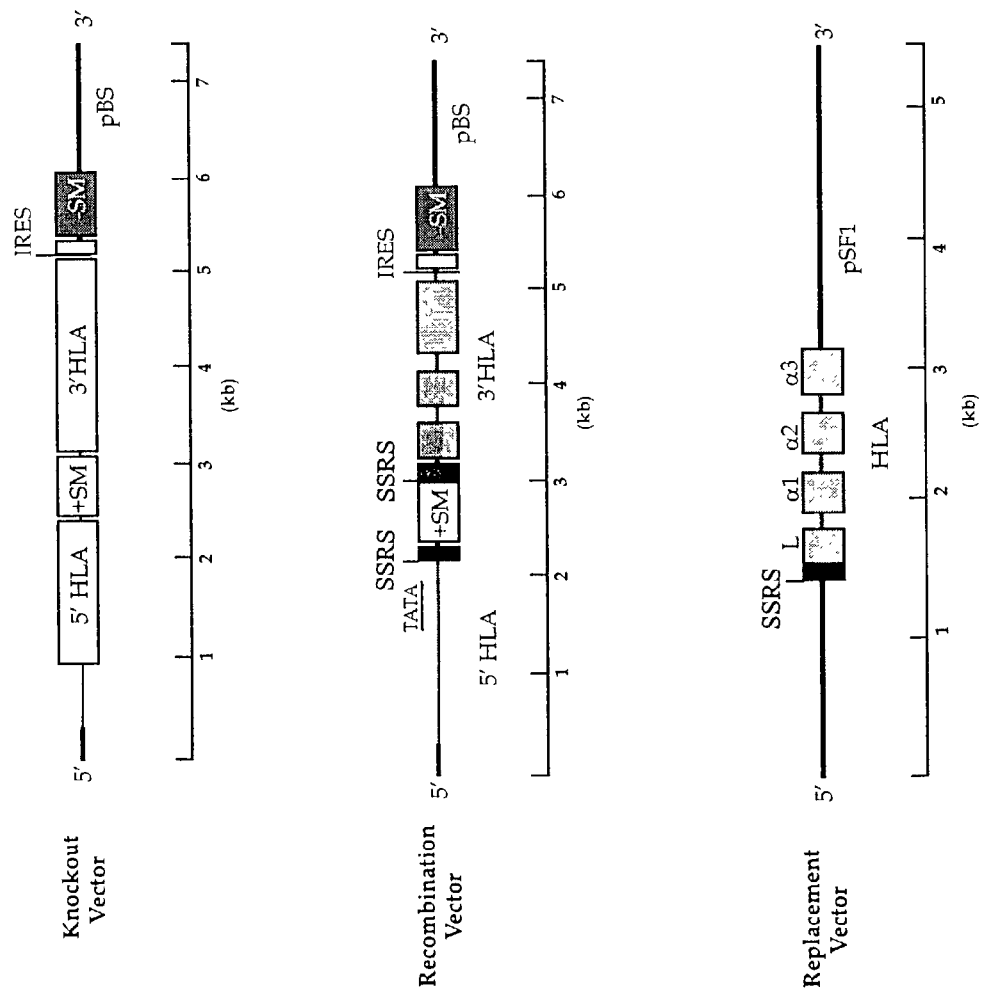
FIG. 6 shows the components of knockout, recombination cassette and replacement vectors. SSRS=site-specific recombination sequence. pBS and pSF are examples of plasmids that can be used.

Blasticidin S (BS), a fungicide widely used in agriculture for the control of rice blast disease, significantly inhibits protein synthesis in both prokaryotes and eukaryotes (Yamaguchi and Tanaka, 1966). A strain of *Aspergillus terreus* (*A. terreus*) inactivates BS by deamination and is highly resistant to the chemical (Yamaguchi et al., 1975). The blasticidin S deaminase gene (bsd) from *A. terreus* was the first drug-inactivating gene of eukaryotic origin used in transformation protocols (Kimura et al. 1994a, Kimura et al., 1994b). The use of bsd provides a reliable and efficient gene transfer system based on selection with BS. Expression of bsd exerts no undesirable effect on the growth of transformed cells. The transformation frequency is as efficient as with the neo gene, which confers resistance to G418 (Kimura et al., 1994b). The use of BS compared with G418, has some important advantages. First, BS strongly and rapidly inhibits cell growth, which saves time during the selection process. The drug, active at small concentrations, is economical. In contrast, the inhibitory effect of G418 is somewhat cytostatic requiring higher concentrations and longer incubation. Second, BS is sufficiently stable in the medium, and yet can easily be inactivated in alkaline solution. As a positive selection marker in the recombination vectors, bsd, is under the control of the polyoma enhancer/tyrosine kinase (TK) promoter, but lacks a polyA signal, and therefore cannot be expressed unless it uses the polyA signal of the HLA gene (see FIG. 5). This marker is placed between two directly repeated loxP sites so that it can be removed from the selected stem cells (Sauer, 1993). The effects of BS on the growth of two types of mammalian cells (STO, a murine feeder cell line and ES D-3, a murine embryonic cell line) and the efficiency of positive selection with BS were studied by subjecting untransfected cells and cells transfected with the bsd gene to different concentrations of the drug. The marker can be removed from the selected stem cells upon transient expression of Cre protein. The system can function in reverse with the insertion of any DNA fragment flanked by loxP sites, through recombination with the existent loxP site in the presence of Cre protein. The site specific recombination cassette was inserted downstream of the transcription initiation site, but upstream of the translation initiation codon. Included at the 3'-end of the primer is a restriction site which will allow insertion of the recombination cassette and selection marker gene. Following removal of the marker, the net change in the genome will be a precise deletion of the coding region of an HLA gene, replaced by a small loxP site.

An intermediate plasmid, pUC/lox/TKpBSD, containing the loxP/bsd cassette was constructed in the following manner. The bsd gene was obtained from pUCSVrevBSD, a kind gift from Dr. Yamaguchi (Riken Institute, Japan). In this plasmid the bsd gene is under the control of the simian virus 40 (SV40) early promoter and has the SV40 polyA sequence attached. However, there were no restriction sites that would allow the separation of the bsd gene from the polyA signal. The current targeting strategy requires that bsd be under control of the polyoma enhancer-TK gene promoter and also be devoid of a polyA sequence. To meet these requirements, the bsd gene was amplified by PCR and then used to replace the neo gene in pMC1neo.pA, which contains the hybrid polyoma enhancer/TK promoter. Convenient restriction sites were engineered in the primers to allow easy separation of the components of the recombinant construct designated pMC1bsd.pA. The bsd gene can be easily separated from the polyA sequence due to the presence of a Sac II restriction site. The pBS246 plasmid (Life Technologies), containing the two direct repeated loxP sites is a low copy number plasmid and, since some of the cloning steps be carried in this plasmid, it was transformed into a high copy number by replacing the pBR322 origin of replication with the origin of replication from pUC19 (New England Biolabs). This plasmid has been designated pUC/loxP. The polyoma enhancer/TK promoter-bsd construct was isolated from pMC1bsd.pA as an Xho I to Sac II fragment and cloned into pUC/loxP. Because neither Xho I nor Sac II are present in the multiple cloning site of pUC/loxP, the polyoma enhancer/TK promoter-bsd construct was first cloned in pGFP-C1 (Clontech) which has a very convenient arrangement of the restriction sites in one of the polylinkers. Plasmids pGFP-C1 and pMC1bsd.pA were digested with Xho I and Sac II and the 750 bp fragment of pMC1bsd.pA and the 4,700 bp fragment of pGFP-C1 were ligated. The resulting plasmid (pGFP/TKpBSD) was digested with Bgl II plus Bam HI and the 760 bp fragment of pGFP/TKpBSD containing the TK promoter and bsd gene was subcloned into the Bam HI site of pUC/loxP in the correct orientation, resulting in a 3.45 kb plasmid designated pUC/lox/TKpBSD.

Negative selection for enrichment of gene targeting events can provided by such markers as thymidine kinase or the diphtheria toxin-A (DT-A) gene. Diphtheria toxin is a naturally occurring toxin synthesized by *Corynebacterium diphtheriae* as a precursor polypeptide that is secreted and enzymatically cleaved into two fragments, designated A and B (Pappenheimer, 1977). The B subunit binds to the surface of most eukaryotic cells, where it is internalized by endocytosis and delivers the A chain into the cytoplasm. DT-A catalyzes the attachment of the ADP-ribose moiety of NAD$^+$ to the elongation factor 2 involved in the growth of the polypeptide chain, thereby inhibiting protein synthesis. Once inside the cell, DT-A is extremely toxic: a single molecule is sufficient to kill a cell (Yamaizumi et al., 1978), but does not exert bystander toxicity to neighboring cells in the absence of the diphtheria toxin B-chain (Maxwell et al., 1986; Palmiter et al., 1987). DT-A was inserted in the vector downstream of the 3'-region of homology with the H2-K$^b$ gene. As a result, the DT-A gene will be expressed only in the event of a non-homologous integration and leads to cell death.

In contrast to the usual mechanism of initiation of translation by ribosome scanning from the 5'-end of the mRNA, the initiation of translation of picornavirus mRNAs, or of any mRNAs bearing a picornaviral 5'-untranslated region (5'-UTR), takes place by a mechanism of internal ribosome entry. This mechanism requires the presence of a defined segment (approximately 600 nucleotides) of the picornaviral 5'-UTR, known as the internal ribosomal entry segment (IRES), which acts as an internal entry point for the cellular ribosomes. IRES-mediated translation is significantly more flexible and efficient than strategies reliant upon promoter-traps or gene-fusions in that when it is integrated into a transcriptionally active gene, production of functional selectable marker and/or reporter protein is expected to be independent of context in the fusion transcript. The fact that IRES function is independent of translation frame or location, greatly simplifies the design and construction of targeting traps (Mountford et al., 1994). In knockout and recombination vectors, the DT-A gene has neither its own promoter nor a polyA signal but is preceded by an IRES in the same orientation as the positive selection marker. This makes the expression of the negative selection marker dependent on both the promoter of the bsd gene and the rare integration events that by chance situate it just upstream of a polyA signal. The advantage of DT-A over other negative selection markers is that it functions simultaneously with positive selection and does not require the addition of drugs which may affect the pluripotentiality of ES cells or other early stem cells.

The negative selection marker construct (pCITE-1.B/DT-A) containing an IRES fused to the DT-A gene was constructed in such a way that the in-frame fusion could be easily utilized in the development of many targeting vectors. pIBI30/DT-A, a gift from Dr. Maxwell (University of Colorado), obtained a mutation during the construction of the plasmid which placed the termination codon out of frame with the DT-A coding sequence. To correct this mutation, the DT-A gene was amplified by PCR using a primer which was designed to introduce two functional termination codons without changing the amino acid composition of the protein, and a Pst I site to be used for further cloning. The amplified DT-A gene was subcloned into the pCRII plasmid. Upon sequence analysis of this plasmid, pAC/DT-A, a one bp insertion immediately following the initiation of transcription was noted. To generate a functional DT-A gene, the correct 5' segment of the gene from pIBI30/DT-A was ligated to the correct 3' segment from pAC/DT-A. The DT-A gene can be isolated as a Nco I/Pst I fragment. The plasmid pCITE-1 (Novagen) carries a copy of the encephalomyocarditis virus RNA 5' non-coding region which functions as an IRES for initiation of translation by eukaryotic ribosomes. This cap-independent translation enhancer (CITE) sequence can be isolated as an Eco RI/Nco I fragment, but the construction strategy requires that a Bam HI site be used. Two Bam HI sites separated by an Xmn I site were introduced into pCITE-1 using Eco RI to Bam HI adapters to generate pCITE-1.B. The coding sequence of DT-A gene was used to generate an in-frame fusion of the DT-A gene with the CITE which can be isolated as a Bam HI/Pst I fragment. Plasmids pDT-A and pCITE-1. B were digested with Nco I plus Pst I. The 600 bp fragment of pDT-A and the 3.7 kb fragment of pCITE-1. B were ligated to form pCITE-1. B/DT-A.

Phase I Knockout Vectors

The construction of the knockout vectors (pKO-B/C and pHKO-DR) will constitute the initial step in the process of developing the universal stem cell of the subject invention. When successful targeting has occurred, the haplotype of these intermediary cell populations will be as shown in Table 4, rows 2&3. Crossovers between large segments of sister chromatids are known to occur during meiosis and may in part be due to the conformation of the DNA in the nucleus. For this reason, it appears that homologous recombination is independent of the distance between regions of homology and can occur between a relatively short targeting sequence and widely spaced regions of the chromosome. The vector, pKO-B/C, will be used to target and excise a region of approximately 100 kb that extends 3 kb upstream of HLA-B and 3 kb downstream from HLA-C on one chromosome (see FIGS. 1, 2, & 3). This is conceivable because HLA-B is adjacent to -C, with no known intervening coding sequences. Similarly, the HLA-DRB genes (1–9) are adjacent to each other. This makes it feasible for pKO-DR to target and delete a region of about 250 kb extending from 3 kb upstream of HLA-DRB1 to 3 kb downstream of HLA-DRB9 (see FIGS. 1, 2 & 3). This will direct the Phase II recombination vectors, pHRC-B/C and pHRC-DR, to target the alleles on the second chromosome. In order to guarantee the greatest chance of homologous recombination, it will be necessary to generate the homology cassettes using DNA from the same population of stem cells being targeted. Primers for PCR amplification of these regions will be generated based on sequences published in GenBank and the human MHC database (MHCDB, available on-line at the HGMP resource centre, Cambridge, UK). Since these homology cassettes are of paramount importance, it will be necessary to experimentally determine both the length and sequence of these regions. This will ensure that we obtain the most efficient targeting vectors possible. Together with these homology cassettes, the following components will be assembled in a pBluescript (pBS) backbone: a positive selectable marker (the green fluorescent protein (gfp) gene in pKO-B/C and the β-galactosidase (lac Z) gene in pHKO-DR), and a negative selectable marker DT-A.

Green Fluorescent Protein. A fully humanized, flow optimized variant of the gfp (hgfp) can be used for positive selection (Heim, et al., 1995) in the pKO-B/C knockout vector (see FIG. 3). The hGFP-S65T gene encodes a mutant gfp which unlike its wild type counterpart, shows a single strong absorption peak at 488 nm, and which can therefore be fully excited by standard argon lasers used in flow cytometers (Zolotukhin et al., 1996) and is less prone to photobleaching than the wild type gfp, making it better suited to flow cytometry applications (Ropp et al., 1995). Furthermore, the hGFP-S65T gene encodes its product using codons that correspond to those preferentially used in mammalian cells, and should direct high level gfp expression suitable for flow detection of gfp-positive cells (Cubitt et al., 1995). The hGFP-S65T gene can be amplified by PCR from the commercially available phGFP-S65T plasmid (Clontech) as a 2.4 kb fragment containing the cytomegalovirus (CMV) 1E early promoter, the hGFP-S65T gene itself, and an SV40 polyA signal. This transcription unit can be amplified using primers that will create appropriate restriction sites at each end of the PCR product and should further enhance levels of gene expression, since the CMV promoter is a very strong mammalian promoter that is highly active in primitive cells.

β-galactosidase. The β-galactosidase (β-gal) encoded by the lac Z gene has been used as a mammalian reporter gene for a number of years, β-gal-expressing cells being identifiable by their ability to convert the chromogenic substrate X-gal (5-bromo-4-chloro-3-indolyl-b-D-galactopyranoside) into a brilliant blue reaction product (Nolan et al., 1988; Berger et al., 1994). It is now possible to detect β-gal activity in live cells by flow cytometry using novel cell permeable b-gal substrates that generate non-toxic, highly fluorescent, yet cell-impermeable reaction products. These b-gal positive cells can be rapidly quantified and sorted as appropriate. A b-gal expression cassette was derived from the 7.5 kb TKb-gal reporter construct (Clontech). This contains a full length bacterial lac Z gene driven by a herpes simplex virus (HSV) TK promoter, and an SV40 polyA signal that will ensure correct RNA processing in mammalian cells. Digestion of pTKb-gal with Sal I restriction endonuclease releases a 4.8 kb fragment containing the complete b-gal transcription unit, which will be used as a positive selection marker in the production of pHKO-DR (see FIG. 3).

Phase II Recombination Vectors

These vectors (pHRC-B/C and pHRC-DR) can be utilized to knockout the remaining HLA-B, -C, and -DR regions on the second chromosome and at the same time, insert a site-specific recombination cassette. The haplotypes of these cells are shown in Table 4, rows 4&5. These successfully targeted stem cells can be cotransfected with pBS185 (Invitrogen), which transiently expresses the Cre protein and pOG44 (Stratagene), which expresses FLP. Cre recombinase will promote recombination between the loxP sites in the chromosomal HRC-B/C, resulting in the excision of the intervening DNA fragment (bsd) and a single loxP site (see FIG. 4, C II). The FLP recombinase will promote recombination between the FRTs in the chromosomal HRC-DR, also resulting in the excision of bsd and a single FRT. Cotransfected cells will be examined for the presence of clones which have become sensitive to BS, indicating that the bsd gene has been deleted. These intramolecular recombinations will complete Phase II and result in the creation of the Universal stem cell of the subject invention (as shown, for example, at Table 4, row 6), Morphogenesis' progenitor line which will be utilized for the creation of an entire bank of haplotype-specific stem cells.

The Phase II strategy requires the construction of several complex targeting vectors incorporating a number of DNA sequences from a variety of sources. The vector, pHRC-B/C, will be used to target and excise a region of approximately 98 kb that extends 1.5 kb upstream of HLA-B transcription initiation and about 1 kb downstream of the HLA-C transmembrane region (see FIGS. 1, 2 & 3). Similarly, pHRC-DR will target and delete a region of about 248 kb extending from 1.5 kb upstream of HLA-DRB1 transcription initiation and about 1 kb downstream of the HLA-DRB9 transmembrane region (see FIGS. 1, 2 & 3). Because Phase I knockouts will have deleted identical target regions on one chromosome, the pHRC-B/C and pHRC-DR homology cassettes will specify the knockout of the HLA-B, -C, and -DRB1–9 regions of the previously untargeted chromosome. As with the Phase I knockout vectors, homology cassettes for Phase II recombination vectors can be generated from genomic DNA isolated from the same population of MS cells used for targeting. Primers for PCR amplification of these regions will be generated based on sequences published in the databases mentioned above. Again, the plasmid backbone can be pBS containing the bacteriophage P1 Cre/loxP site-specific recombination cassette, variant loxP sites, or the comparable FRT/FLP system from yeast flanking the bsd gene, and the DT-A negative selection marker.

The strategy described above for the deletion of the HLA-B, -C and -DRB1–9 regions requires the deletion of large segment of DNA sequence. An alternative method to achieve the precise excision of a genomic DNA sequence would be the introduction, by homologous recombination, of two loxP sites, one 5' to one of the targeted genes (HLA-B) and the other 3' to the second targeted gene (HLA-C). Following the integration of the loxP targeting vectors, purified Cre recombinase protein can be introduced into the cells to catalyze the site specific recombination at the loxP sites resulting in the excision of the intervening DNA sequence and one of the loxP sites (Baubonis and Sauer, 1993). As stated by Baubonis and Sauer (1993) the use of the purified Cre recombinase protein rather than the transient expression of the cre gene, not only eliminates the requirement for a co-transfecting cre expression vector but also the possibility of unwanted integration of the cre gene elsewhere into the targeted genome.

TABLE 4

Haplotypes and phenotypes of genetically targeted stem cells.

| Manipulation | Haplotype | Phenotype |
| --- | --- | --- |
| 1. Stem Cell | A2 B+ C+ DR+ / A2 B+ C+ DR+ | $A^{hi}$ $B^{hi}$ $C^{hi}$ $DR^{hi}$ GFP− βgal− $BSD^s$ |
| 2. KO B/C | A2 B− C− DR+ / A2 B+ C+ DR+ | $A^{hi}$ $B^{lo}$ $C^{lo}$ $DR^{hi}$ GFP+ βgal− $BSD^s$ |
| 3. KO DR | A2 B− C− DR− / A2 B− C− DR+ | $A^{hi}$ B− C− $DR^{lo}$ GFP+ βgal+ $BSD^s$ |
| 4. RC B/C | A2 B− C− DR+ / A2 B− C− DR+ | $A^{hi}$ B− C− $DR^{hi}$ GFP+ βgal− $BSD^r$ |
| 5. RC DR | A2 B− C− DR− / A2 B− C− DR− | $A^{hi}$ B− C− DR− GFP+ βgal+ $BSD^r$ |
| 6. Cre/FLP[1] | A2 B− C− DR− / A2 B− C− DR− | $A^{hi}$ B− C− DR− GFP+ βgal+ $BSD^s$ |
| 7. RE B44 | A2 B44 C− DR− / A2 B− C− DR− | $A^{hi}$ B44 C− DR− GFP+ βgal+ $BSD^s$ |
| 8. RE DR7 | A2 B− C− DR7 / A2 B− C− DR− | $A^{hi}$ B− C− DR7 GFP+ βgal+ $BSD^s$ |
| 9. RE B44/DR7 | A2 B44 C− DR7 / A2 B− C− DR− | $A^{hi}$ B44 C− DR7 GFP+ βgal+ $BSD^s$ |
| 10. RE B44/DR7 | A2 B44 C− DR− / A2 B− C− DR7 | $A^{hi}$ B44 C− DR7 GFP+ βgal+ $BSD^s$ |

1 = Universal stem cell of the subject invention
KO = knockout
RC = recombination
RE = replacement Bacteriophage P1 Cre-loxP Site-Specific Recombination System. The Cre protein encoded by coliphage P1 is a 38 kDa protein that efficiently promotes both intra- and intermolecular recombination of DNA. Recombination occurs at specific 34 bp sites called loxP, and does not require any other protein factors (Sauer and Henderson, 1988). Recombination between two directly oriented loxP sites on the same molecule excises the intervening DNA segment as a circular molecule having a single loxP site. The intermolecular recombination between a circular DNA molecule carrying a single loxP site and a DNA molecule containing a loxP site results in integrative recombination but is less efficient than the intramolecular event (Sauer, 1993). Both intra- and intermolecular recombination are catalyzed by Cre with either supercoiled or linear DNA. The 34 bp loxP site consists of two 13 bp inverted repeats, binding sites for the Cre protein, and an 8 bp asymmetric core region in which recombination occurs and which is responsible for the directionality of the site (Hoess and Abremski, 1984). Sites in direct orientation on a DNA molecule dictate excision of the intervening DNA between sites; sites in opposite orientation to each other invert the intervening DNA segment on Cre-mediated recombination. An intermediate plasmid containing the bsd gene flanked by two loxP sites, pUC/lox/TKpBSD, was constructed for use in both mouse and human recombination cassette vectors. This high copy number plasmid will yield a directional loxP/TKbsd recombination cassette when digested with various combinations of restriction endonucleases (Not I or Eco RI with either Spe I, Sfi I, or Not I) which will then be incorporated into pHRC-B/C (see FIG. 3).

Yeast FLP-FRT Site-Specific Recombination System. The pHRC-DR recombination cassette can contain two FRT site-specific recombination sequences flanking bsd (see FIG. 3). The FRT consists of two inverted 13 bp repeats and an 8 bp spacer (O'Gorman, et al., 1991). Two FRTs from pNEOβGAL plasmid (Stratagene) can be used to flank the bsd gene. Bsd, under the control of the TK promoter can be readily obtained from pMC1bsd.A by digestion with Xho I and Sac II or from pGFP/TKpBSD with Bam HI and Bgl II. Alternatively, heterospecific lox sites could be utilized (Sauer 1996). These variant lox sites, having an altered spacer region are not proficient for Cre-mediated recombination with the canonical 34 bp loxP site, but can recombine with each other. By placing different heterospecific lox sites on different alleles, Cre can catalyze independent DNA recombination events at multiple loci in the same cells.

Phase III Replacement Vectors

The simple design of the Phase III constructs calls for vector backbone such as pBS backbone. To generate the pHRE-B(44) vector, the replacement gene, HLA-B44 will be cloned into pSF1 (Life Technologies) adjacent to the single loxP site. To generate the pHRE-DR(7) replacement vector (see FIG. 3), the replacement allele, HLA-DR7, would be directionally cloned into a choice of Kpn I, Xho I, Hinc II, Cla I, or Hind III sites upstream of the FRT in the pOG45 targeting vector (Stratagene). In the second exposure to Cre, the loxP site of pHRE-B(44) replacement vector will recombine with the single loxP site remaining in the altered HLA-B/C region of chromosome 6, resulting in the replacement of the deleted HLA-B and -C alleles with B44 (see FIG. 4). Similarly, in a second exposure to FLP, the FRT site of pHRE-DR(7) replacement vector will recombine with the single FRT previously inserted in the HLA-DR region of chromosome 6 by pHRC-DR, resulting in the insertion of HLA-DR7.

In contrast to mouse ES cell lines, nontransformed human cells have a finite life-span in vitro. This makes their modification by gene targeting especially challenging (Williams et. al., 1994). It is also important to remember that the structure and behavior of each individual locus, as well as the particular genetic modification required, will dictate the type and design of the targeting vector (Bronson and Smithies, 1994), an issue that can only be addressed once the vectors are transfected into stem cells. Under optimal conditions for homologous recombination, double targeting events might occur in the same cell, provided multiple vector types were present. Therefore, in addition to single transfections with each Phase I knockout vector, pKO-B/C and pKO-DR can be introduced into stem cells simultaneously. Double knockout cells will be GFP$^+$ β-gal$^+$ and HLA-B, -C and -DR hemizygous deleted. If successful, these hemizygous cells will be cotransfected with pHRC-B/C and pHRC-DR. Cells will be GFP$^+$ β-gal$^+$, BSD$^r$, and HLA-B, -C, -DR null, if another double targeting event has occurred. The generation of this cell in two steps would greatly facilitate the use of the subject invention on other stem cell types, reducing the risk of losing multipotentiality or otherwise impairing normal functions.

It is anticipated that by increasing the number of stem cells transfected, optimizing DNA uptake and implementing an highly efficient screening strategy, it will be possible to optimize the absolute targeting frequency. High efficiency selection markers will be utilized together with FACS, to rapidly process large numbers of cells and isolate correctly targeted cells. The level of MHC class I and II surface expression can be experimentally determined in undifferentiated and differentiated stem cells and will be utilized in FACS selection. A further refinement made possible by FACS is the use of a single cell deposition unit to isolate single cells thought to have undergone targeting. Clonal expansion of single cells in a multi-well format greatly simplifies subsequent genetic analyses, and allows one to directly quantitate targeting efficiencies under different experimental conditions. Fidelity of targeting in cells initially identified by flow cytometry as having undergone homologous recombination, can be verified after clonal expansion by a combination of PCR and Southern analysis.

It is generally possible to distinguish homozygous from hemizygous MHC-positive cells by the intensity of the surface fluorescence. Therefore, knockout clones can be identified by the reduced intensity of the MHC labeling as well as by the expression of hGFP-S65T for the pHKO-B/C vector or b-gal for the pHKO-DR vector. Cells among the GFP/βgal-positive knockout population that have undergone illegitimate random integration should express the MHC alleles at normal or high levels. In contrast, cells that have undergone homologous recombination, are hGFP-S65T/β-gal-positive and MHC dull or low (see Table 4, rows 2&3). Bsd resistant recombination competent stem cells targeted by either pHRC-B/C or pHRC-DR will be -B/C and -DR null, respectively (see Table 4, rows 4&5). Cells whose MHC alleles have been correctly targeted and replaced by the site-specific recombination vectors pHRE-B(44) and pHRE-DR(7) can be identified by antibodies against each of those specific antigens. Correctly targeted cells can be positively sorted using an automatic single cell deposition unit. In this way, single cells identified as having been correctly targeted can be deposited directly into individual wells of 96-well tissue culture plates, and clonally expanded prior to further analysis. As described below, SC-1 cells stably expressing the β-gal and hGFP-S65T genes can be used as positive controls to ensure efficient marker detection.

Transfection of ES Cells

The vectors can be introduced into ES cells by electroporation. Embryonic stem cells can be grown to a density of $2 \times 10^7$ cells per 100-mm culture dishes in nonselective medium. The cultures can be harvested, centrifuged, and resuspended in nonselective medium to a density of $10 \times 10^7$ cells per ml. Prepared vector DNA can be added to a final concentration of 5 nM to 400 ml cell suspension and incubated on ice for 20 min. The mixture can be loaded into a 4 mm gap electroporation cuvette, and pulsed for 1 sec at 250 mF charged to 300 V. The cells should be removed immediately from the chamber and plated onto confluent layers of $BSD^r$ feeder cells where they will be allowed to recover overnight before BS selection media is applied.

A double flow selection strategy can then be employed to identify and isolate potentially targeted cells. Flow analysis of transfected cells can begin 24–72 hours post-transfection to allow expression of selectable markers. It may be necessary to divide each transformed ES clone into two parts, one will be maintained undifferentiated, the other will be allowed to begin differentiation. Primitive ES cells sometimes do not express MHC I genes, however, once differentiation has been initiated, expression occurs. MHC expression can also be monitored by flow cytometry using monoclonal antibodies. All cell labeling should be carried out according the manufacturer's instructions.

Embryonic stem cells, successfully targeted with vector DNA, can be cotransfected with pBS185 (Invitrogen), which transiently expresses the Cre protein or with the Cre protein itself. Cre recombinase will promote recombination between the loxP sites in the chromosomal recombination vector, resulting in the excision of the intervening DNA fragment (bsd) and a single loxP site (see FIG. 4, C II). To generate the replacement vectors, a heterologous HLA genes can be cloned into pSF1 (Life Technologies) adjacent to the single loxP site (see FIG. 3). In the second exposure to Cre, the loxP site of the replacement vector recombines with the single loxP site remaining in the altered HLA region, resulting in the replacement of the deleted HLA allele with the desired one (see FIG. 4, III C).

Isolation and Maintenance of Mesenchymal Stem Cells

Bone marrow aspirates (50 ml) can be obtained from a healthy individual of HLA-A2, for example, haplotype A*0201 allele, using standard clinical procedures. Following the removal of bone chip particles the cells can be applied to a Percoll density gradient according to the procedures described by Haynesworth et al., 1992. The MS cells, recovered at approximately 1.03 g per ml, will be collected by centrifugation and resuspended in Dulbecco's Modified Eagle's Medium (DMEM) supplemented with 10% (v/v) heat-inactivated fetal bovine serum (FBS) and seeded into tissue culture plates. Most hematopoietic cells remain in suspension while the MS cells selectively adhere to the plates. Suspended cells can be removed by aspiration, adherent cells will be maintained in DMEM supplemented with 10% FBS. Between 5,000 and 7,500 MS colonies are expected to be recovered using this procedure. These cells can be passaged in vitro for over 30 population doublings without loss of assayable osteogenic activity.

Transfection of Mesenchymal Stem Cells

The current method of choice for transfecting cells for evidence of homologous recombination is electroporation. However, if transfection by electroporation is insufficient, other transfection systems such as lipids, dendrimers, DEAE-dextran, nuclear injection, particle bombardment, can be used. For electroporations, semi-confluent cells can be harvested, centrifuged, washed, and resuspended in sterile DMEM plus 10% FBS to approximately $5 \times 10^6$ cells per ml. Given the best transformation and targeting frequencies expected and calculating the number of divisions a cell will have to get through the whole process, it is estimated that this is a sufficient number of MS cells for each round of transfection. In a 4 mm gap electroporation cuvette, 400 ml cell suspension will be mixed with 10 mg linearized plasmid DNA and pulsed at between 950 and 1050 mF, variable voltage and infinite internal resistance. For optimization of the voltage, 20 V increments in the range 240–300 V can be used. The cells will be collected immediately in 5–10 ml of complete DMEM by rinsing the cuvette twice with medium and plated in a T-75 flask and allowed to recover prior to the addition of BS selection media and/or FACS analysis.

Flow Cytometry

Expression of β-gal can be detected by flow cytometry using the DetectaGene Blue reagent system (Molecular Probes). Cells can be loaded with the chromogenic β-galactosidase substrate 4-chloromethylcoumarin-b-D-galactopyranoside by isotonic shock, according to manufacturer's instructions. Cells expressing β-gal will convert this substrate into a highly fluorescent reaction product that will be excited using a 363 nm UV laser line, and fluorescence will be monitored between 440 and 540 nm (1 max=470 nm). Expression of the hGFP-S65T marker can be determined more directly, since it exhibits intrinsic fluorescence. This particular gfp variant carries a serine to threonine mutation at amino acid position 65, which results in it having a single strong absorption peak at 490 nm, allowing optimal excitation with an argon laser line at 488 nm, however other variants may be used. GFP fluorescence of this variant can be detected between 500 and 535 nm, essentially as for detection of fluorescein isothiocyanate (FITC) label. The frequency of targeted recombination in initial targeting experiments is expected to be very low. Therefore, it is important to ensure that expression of the flow selectable marker genes does indeed occur in target cells, and that their expression can be detected by flow cytometry with sufficient sensitivity. For this reason, SC-1 cells which stably express hGFP-S65T (pBS BSD/hGFP) or lac Z (pBS BSD/β-gal) have been established. MHC expression can also be monitored by flow cytometry using the such monoclonal antibodies as; 0289HA (HLA-A1, A36), 0601HA (B44,B75, B17+), 0757AHA (DR7+), Goat anti-human IgM FITC (One Lambda) and anti-HLA-DR PE (Monomorphic).

Confirmation of Targeting Events

Knockouts and gene replacements can be confirmed in flow sorted cells. It is critically important to demonstrate that the constructs can target the appropriate locus, and that the flow selection strategy can identify correctly targeted cells. It is also necessary to determine how many illegitimate recombinants, and non-recombinants, escape negative selection. Random integration of a damaged targeting construct with a silenced negative selection marker, or integration into a transcriptionally silent locus will generate false positives. For subsequent experiments examining targeting efficiency, it is important to determine the level of this untargeted background. The genomic structure of the targeted event can be confirmed by PCR amplification. Two primer pairs can be used, each consisting of a primer specific for sequences flanking the targeted region yet outside of the targeting construct itself, and a primer specific for a region within the targeting construct's positive selection marker. These primer pairs only generate PCR products of predictable sizes when the targeting construct has integrated correctly, and become flanked by primer-specific genomic sequences. Since one of the genome-specific primers can be designed to anneal 5' to the targeted region, and the other 3' to it, this approach will confirm correct integration of both ends of the targeting construct. If required, PCR products can be Southern blotted, and probed with targeting construct-specific probes derived from restriction fragments, in order to confirm specificity of PCR amplification.

Functional Assay for MS Cell Differentiation

An in vitro assay, to measure differentiation of MS cells has been developed based on that described by Farley et al. (1991). This assay measures alkaline phosphatase-specific activity as an index of osteogenic differentiation. Briefly, MS cells can be resuspended at varying concentrations in DMEM supplemented with 10% FBS, varying concentrations (5–20 ng per ml) of epidermal growth factor with and without NaF, $10^{-6}$ M. Cells are incubated at 37° C. in an atmosphere of 5% $CO_2$ in air for a period of seven to ten days. Following incubation, the cultures can be assayed for alkaline phosphatase activity (Farley et al., 1991). This assay has been standardized using normal MS cells and the osteosarcoma cell line, SAOS-2.

In Vitro CTL and NK Cell Assays

CTL assays can be performed by incubating various numbers of effector cells, generated in mixed lymphocyte cultures for 5–6 days, with $2\times10^{3-51}$ Cr-labeled target cells for 4 hr. Mixed lymphocyte cultures can be set up in 24-well plates (2 ml per well) and can consist of responder spleen cells ($4\times10^6$–$6\times10^6$ per well) and gamma irradiated (200 rad) stimulator cells ($4\times10^6$–$6\times10^6$ per well). NK cell assays can be performed with spleen cell effectors from untransplanted mice and $2\times10^{3-51}$ Cr-labeled targets for 6 hr. in U-bottom microtiter plates. Red blood cells can be removed from the effector population by hypotonic saline lysis.

Materials and Methods

Cell Culture

Cell cultures can be maintained at 37° C., in a humidified atmosphere of 5% $CO_2$ in air. In preparation for use, subconfluent cells will be harvested, centrifuged, washed, resuspended in sterile DMEM and counted to determine viable cell numbers using trypan blue exclusion.

DNA Isolation

To isolate genomic DNA, cells can be collected under sterile conditions and placed in sterile DMEM. The harvested cells can be transferred to a 15 ml conical centrifuge tube and centrifuged for 5 minutes at 4000×g and 4° C. The supernatant can be removed and the pelleted cells resuspended in 3 ml sterile distilled water to rapidly lyse the erythrocytes; 12 ml of sterile DMEM should be immediately added to prevent the lysis of the leukocytes. The cells can be collected and genomic DNA extracted following any method currently available The method of Herrmann and Frischauf (1987) is described here. Bacteria carrying recombinant plasmids are grown on agar plates containing the appropriate selection antibiotic(s). Individual colonies should be used to inoculate small volumes (3 or 5 ml) of Luria-Bertani (LB) broth (1% (w/v) tryptone, 0.5% (w/v) yeast extract, 0.5% (w/v) NaCl, 0.001N NaOH) containing the appropriate selection antibiotic(s) and grown to saturation. Large amounts of plasmid DNA can be prepared by alkaline lysis using QIAGEN Maxi Plasmid Purification Kit (Qiagen Inc.) following the protocol supplied by the manufacturer. Alternatively, standard alkaline lysis of bacteria will be used, followed by purification of plasmid DNA by cesium chloride gradient. For small-scale isolation of plasmid DNA, The plasmid DNA can be isolated by standard alkaline lysis miniprep procedure (Ausubel et al., 1989). The DNAs can be detected using agarose gel electrophoresis. Specificity of detection should be based upon size of the expected plasmid compared to a supercoiled DNA ladder (Life Technologies). Gels can be 0.7% (w/v) agarose in 1×TAE buffer and run at 5 volts per centimeter length for 120 minutes. Ethidium bromide can be included at a concentration of 0.5 mg per ml in the gels but not in the TAE running buffer.

Polymerase Chain Reaction

PCR can be used to generate the 5'- and 3'-regions of homology to the HLA-B, -C, and -DR alleles to be targeted. The sequence analyses and primer design is computer assisted. The structure and internal stability of the primers and amplification products can be analyzed using the program Oligo(National Biosciences, Inc.) and the selected primers can be synthesized by Oligos Etc. Based on the sequence analyses of the MHC genes generated with the programs such as GeneWorks (IntelliGenetics Inc.), primers can be designed to take advantage of the nonhomologies between the allelic sequences. The PCR reactions should be carried under the conditions appropriate for each type of reaction and can be determined by 'trial and error'. However, in general the materials used can be: 5 U per ml Taq DNA polymerase (Promega), Taq DNA polymerase buffer 10×(500 mM KCl, 100 mM Tris-HCl, pH 9, 1% Triton X-100), nucleotide solution (25 mM each, dATP, dCTP, dGTP, and dTT) (Pharmacia Biotech Inc.), 5' and 3' primers (100 mM each), 25 mM $MgCl_2$, and sterile ultrapure water. The PCR amplifications can be performed in a GeneAmp 9600 PCR System (Perkin Elmer Corporation) with the following settings: 1 cycle at 94° C. for 5 minutes; 35 cycles at 94° C. for 30 seconds, 56° C. or 62° C. for 30 seconds, 72° C. for 90 seconds and 1 cycle at 72° C. for 10 minutes, followed by cooling to 4° C.

Subcloning Procedures

Restriction endonuclease digestions can be used to isolate the DNA fragments of interest from larger DNA molecules for further procedures or to determine the identity of the insert in the recombinant plasmids and should be carried out in accordance with the manufacturer's instructions and with the appropriate buffers. Ligation of DNA fragments by joining their ends, either cohesive or blunt, with T4 DNA ligase, can be used to generate recombinant DNA molecules. The efficiency of a ligation is dependent on the concentration of DNA in the reaction and on the insert: vector molar ratio and must be determined experimentally for each reaction. In general, ligations can be performed as follows; 250 ng lyophilized vector and insert DNA (molar ratio to be determined), 0.25 ml T4 DNA ligase (20 Weiss U per ml), 0.5 ml T4 DNA ligase buffer 10×(300 mM Tris-HCl pH 7.8, 100 mM MgCl2, 100 mM dithiothreitol, 10 mM adenosine-triphosphate, 0.5 ml acetylated bovine serum albumin, 10 mg per ml, and sterile water to 5 ml. The ligation reactions should be incubated at 14° C. for 18 hr. and stopped by heating at 75° C. for 10 minutes.

TA cloning technique allows the direct insertion of a PCR product into a plasmid vector without any enzymatic manipulations and contains the lac Za complementation fragment for blue-white color screening. When multiple subcloning step are involved in the production of genetic vectors, it is sometimes advantageous to use this interim step, even when PCR primers have been designed to give the product relevant restriction endonuclease recognition sites located at the ends of the product. Using the TA Cloning Kit (Invitrogen), PCR-amplified gene fragments can be cloned into pCRII vector as per manufacturer's instructions.

Transformation of Bacteria

Transformation by electroporation with high voltage can be used to introduce recombinant DNA molecules into competent bacteria. The strains of *Escherichia coli* suggested for the transformation experiments are DH5a and DH10B even though others could be used. Aliquots of electrocompetent bacteria (50 ml) can be mixed with 50 ng DNA from a ligation reaction. The mixture is then transferred to a 2 mm gap prechilled electroporation cuvette (BioRad), inserted into the sample chamber, and subjected to a very short electrical pulse. The Gene Pulser can be set to 2.5 kilovolts, 21 mF, and the wave controller to 400 ohms, for example. Following electroporation, bacteria can be diluted with 1 ml prewarmed medium such as SOC (0.5% yeast extract, 2% tryptone, 10 mM NaCl, 2.5 mM KCl, 10 mM $MgCl_2$, 20 mM $MgSO_4$, 20 mM glucose), transferred to sterile culture tubes and shaken vigorously for 1 hr at 37° C. The bacteria can then be plated on LB agar containing the appropriate selection antibiotic(s).

Probes

Different procedures can be used for labeling DNA probes, two are described here: 1) The appropriate DNA will be labeled with Redivue [($^{-32}$P] dCTP at 10 mCi per ml (Amersham Life Sciences), using the Rediprime DNA labeling kit (Amersham Life Sciences), according to manufacturer's instructions. Unincorporated nucleotides will be removed using a ProbeQuant G-50 sephadex column (Pharmacia Biotech), and 2) The PCR-amplified products will be labeled with Redivue [($^{-32}$P] dATP (10 mCi per ml), using the Prime-It II Random Primer Labeling Kit (Stratagene) according to manufacturer's instructions. The unincorporated nucleotides will be removed as above.

It should be understood that the examples and embodiments described herein are for illustrative purposes only and that various modifications or changes in light thereof will be suggested to persons skilled in the art and are to be included within the spirit and purview of this application and the scope of the appended. All references cited herein are hereby incorporated by reference in their entirety.

References

Armstrong, J. W., Simske, S. J., Beharka, A. A., et al. (1994). J. Leukocyte Biol. 55, 658.

Auchincloss, H. (1988). Transplant. 45, 1.

Ausubel, F. M., Brent, R., Kingston, R. E., et al. (1993). In *Current Protocols in Molecular Biology* eds. (Wiley & Sons Inc., New York, N.Y.).

Baubonis, E., and Sauer, B., (1993) Nucleic Acids Research 21, 2025.

Benichou, G., Tam, R. C., Soares, L. R. B., et al. (1997). Immunology Today 18, 67.

Bidwell, J. (1994). Immunology Today 15, 303.

Bollinger, R. R. and Sanfilippo, F. (1989). In *Principles of Organ Transplantation*. M. W. Flye, ed. (W. B. Saunders, Philadelphia, Pa.) p 47.

Berger, C. N., Seong-Seng, T., and Sturm, K. S. (1994). Cytometry 17, 216.

Bradley, A., Evans, M., Kaufman, M. H., and Robertson, E. J. (1984). Nature 309, 255.

Bronson, S. K. and Smithies, O. (1994). J. Biol. Chem. 269 (44), 27155.

Browning, M. and Krausa, P. (1996). Immunol. Today 17 (4), 165.

Capecchi, M. R. (1994). Scientific American March 52.

Caplan, A. I., and Bruder, S. P. (1997). In *Principles of Tissue Engineering*. Lanza, R., Langer, and Chick, W. eds. (R. G. Landes Co., Austin, Tex.) p 603.

Carlow, D. A., Payne, U., Hozumi, N., et al. (1990). Eur. J. Immunol. 20, 841.

Chang, T., (1995). Artificial Organs 16, 71.

Corry, R. J., and Russell, P. S. (1973). In *Immunolgical Sspects of Transplantation Surgery*. Wiley, New York, N.Y., p 279.

Cubitt, A. B., Heim, R., Adams, et al. (1995). Trends Bio. Sci. 20, 448.

David-Watine, B., Israel, A., and Kourilsky, P. (1990). Immunol. Today 11, 286.

Danet-Desnoyers, G., Lane, T., Lawman, P. D. et al., (1995). ASH.

Donahue, R. E., Kessler, S. W., Lawman, M. J. P., et al., (1992). ASH.

Drezen, J. M., Nouvel, P., Babinet, C., and Morello, D. (1992). J. Immunol. 149, 429.

Dyer and Middleton

Ellis, T. M. (1994). In *The Role of MHC and Non-MHC Antigens in Allograft Immunity*. LT. Mohanakumar ed. (T. G. Landes Co., Austin, Tex.) p 27.

Evans, M. J. and Kaufman, M. H. (1981). Nature 292, 154.

Farley, J. R., Hall, S. L., Herring, S., et al. (1991). Metabolism 40, 664.

Faustman, D. and Coe, C. (1991). Science 252, 1700.

Faustman, D. (1995). Trends in Biochem. Tech. 13, 100.

Galli-Taliadoros, L. A., Sedgwick, J. D., Wood, S. A., et al. (1995). J. Immunol. Methods 181, 5.

Goss, J. A., Nafakusa, Y., Yu, S., et al. (1993). Transplant. 55, 166.

Haynesworth, S. E., Baber M. A., and Caplan, A. E. (1992). Bone 13, 69.

Heim, R., Cubitt, A. B., and Tsien, R. Y. (1995). Nature 373, 663.

Herrmann, B. G., and Frischauf, A. (1987). Methods in Enzymol. 152, 180.

Hoess, R. H. and Abremski, K. (1984). Proc. Natl. Acad. Sci. USA 81, 1026.

Ishikawa, Y., Tounaga, K., Tanaka, H., et al., (1995). Immunogenetics 43, 1.

Isobe, M., Yagita, H., Okumura, K., et al. (1992). Science 255, 1125.

Izumi, M., Miyazawa, H., Kamakura, T, et al., (1991). Exp.Cell Res. 197, 229.

Joyner, A. L., Skarnes, W. C., and Rossant, J. (1989). Nature 338, 153.

Karre, K., Ljunggren, H. G., Piontek, G., et al. (1986). Nature 319, 675.

Kim, M., Duty, L., Herberman, R., et al. (1994). Cell Immunol. 155, 358.

Kimura, M., Kamakura, T., Tao, Q. Z., et al. (1994a). Mol. Gen. Genet. 242, 121.

Kimura, M., Takatsuki,A., and Yamaguchi, I. (1994b). Biochim. Biophys. Acta. 1219, 653.

Klein, J. (1986). In *Natural History of the Major Hisotcompatibility Complex*. Wiley & Sons, Inc. New York, N.Y. p 23.

Lanza, R. P., and Soon-Shiong, P. (1991). In *Xenotransplantation* p 297.

Lanza, R. P., and Chick, W. L., (1997). In *Principles of Tissue Engineering*. R. P. Lanza, R. Langer, and W. L. Chick eds. (Academic Press and R. G. Landes Company, Austin, Tex.) p 405.

Lawman, M. J. P., Wathana, S., Donahue, R. E., et al., (1992). Blood 80:149a, Suppl. I.

Lawman, M. J. P., Denslow, N., Qiu, L., et al., (1995). AACR.

Lechler, R. I., and Batchelor, J. R., (1982). J. Exp. Med. 155, 31.

Markmann, J. F., Campos, L., Bhandoola, A., et al. (1994). Surgery 116, 242.

Mansour, S. L., Thomas, K. R. and Capecchi, M. R. (1988). Nature 336, 348.

Maxwell, I. H., Maxwell, F., and Glode, L. M. (1986). Cancer Res. 46, 4660

Mountford, P., Zevnik, B., Duwel, A., et al. (1994). Proc. Natl. Acad. Sci. USA 91, 4303.

Musk, P., Lawman, M. J. P., Lawman, P. D., et al., (1995). ASH.

Newell, W. R., Trowsdale, J., and Beck, S. (1996). Immunogenetics 45, 6.

Nolan, G. P., Fiering, S., Nicolas, J. F., and Herzenberg, L. A. (1988). Proc. Natl. Acad. Sci. USA 85, 2601.

O'Gorman, S., Fox, D. T., Wahl, G. M., (1991). Science 251, 1351.

Palmiter, R. D., Behringer, R. R., Quaife, C. J., et al. (1987). Cell 50, 435.

Pappenheimer, A. M. Jr. (1977). Ann. Rev. Biochem. 46, 69.

Pearson, T. C., Madfsen, J. C., Larsen, C. P., et al. (1992). Transplant. 54, 475.

Peelman, L. J., Chardon, P., Vaiman, M., Mattheeuws, M., Van Zeuren, A., Vande Weghe, A., Bouguet, Y., Campbell, R. D., (1996) Mamm Genome 7:363–367.

Qian, S., Fung, J., Demetris, A. et al. (1991). Transplant. 52, 562.

Regalado, A. (1996). Start-Up. November p20.

Ropp, J. D., Donahue, C. J., Wolfgang-Kinball, D., et al. (1995). Cytometry 21, 309.

Sauer, B (1996) Nucleic Acids Research 24:4608.

Sauer, B., (1993). Methods Enzymol. 225, 890.

Sauer, B. and Henderson, N. (1988). Proc. Natl. Acad. Sci. USA 85, 5166.

Sell, S. (1996a). Immunomodulation. In *Immunology, Immunopathology & Immunity*. Sell, S. Berkower, I., and Max, E. E. eds. (Appleton & Lange, Stamford, Conn.) p 821.

Sell, S. (1996b). Transplantation. In *Immunology, Immunopathology & Immunity*. Sell, S. Berkower, I., and Max, E. E. eds. (Appleton & Lange, Stamford, Conn.) p 588.

Shim et al. (1997) Biol. Reprod. 57, 1089.

Siebers, U., Zekorn, T., Bretzel, R. G., et al. (1990). Transplant. Proc. 22, 2035.

Sidney, J., Grey, H. M., Kubo, R. T., and Sette, A. (1996). Immunol. Today 17 (6), 261.

Spencer Wells, R., and Parham P. (1996) pp. 77–79.

Stange, J., Mitzner, S., et al. (1993). Biomat. Artif. Cell & Immob. Biotech. 21, 343.

Stange, J., and Mitzner, S., (1996). Internat. J. Artif. Organs 19, 45.

Schwartzberg, P. L., Goff, S. P., and Robertson, E. J. (1989). Science 246, 799.

Smithies, O., Gregg, R. G., Boggs, S. S., et al. (1985). Nature 317, 230.

Sullivan, J. A., Oettinger, H. F., Sachs, D. H., Edge, A. S., (1997) J. Immunol. 159:2318–2326.

Sykes, M., Aksentijevich, I., and Sharabi, Y., et al. (1991). In *Xenotransplantation* p 121.

Tellier, M. C., Lawman, M. J. P., and Lawman, P. D. (1993). Int. Soc. Hem. and Graft Eng.

Te Riele, H., Maandag, E. R., and Berns, A. (1992). Proc. Natl. Acad. Sci. USA 89, 5128.

Thomas, K. R., and Capecchi, M. R. (1987). Cell 51, 503.

Thomson, J. A. and Marshall, V. S. (1998) Curr Top Dev Biol 38,133.

Thomson et al. (1996) Biol Reprod 55, 254.

Thomson et al. (1995) Proc. Natl. Acad. Sci. USA 92, 7844.

VanBuskirk, A. M., Brown, D. J., Adams, P. W., et al. (1994). In *The Role of MHC and Non-MHC Antigens in Allograft Immunity*. T. Mohanakumar ed. (R. G. Landes Co., Austin Tex.) p. 27.

Velten, F., Rogel-Gaillard, C., Renard, C., Pontarotti, P., Tazi-Ahnini, R., Vaiman, M., Chardon, P., (1998) Tissue Antigens 51:183–194.

Wheeler, M. B. (1994) Reprod. Fertil. Dev. 6,563.

Williams, S. R., Ousley, F. C., Vitex, L. J., et al. (1994). Proc. Natl. Acad. Sci. USA 91, 11943.

Wong, W., Morris, P. J., and Wood, K. J., (1996). Transplant. 62, 1462.

Yamaguchi, H. and Tanaka, N. (1966). J. Biochem. 60, 632.

Yamaguchi, I., Shibata, H., Seto, H., and Misato, T. (1975). J. Antibiot. 28, 7.

Yamaizumi, M., Mekada, E., Uchida, T., and Odaka, Y. (1978). Cell 15, 245.

Zhang, Z, Zhu, L., Quan, D., et al., (1996). Transplant. 62, 1267.

Zolotukhin, S., Potter, M., Hauswirth, W. M., et al. (1996) J. Virol. 70, 4646.

We claim:

1. An in vitro method of altering the histocompatibility phenotype of a human stem cell, comprising:
    a) deleting adjacent HLA-B and HLA-C MHC genes from a first chromosome;
    b) replacing HLA-B and HLA-C MHC genes on a second chromosome with a site specific cassette, said cassette comprised within a vector that includes a site specific recombination sequence selected from LoxP and FRT;
    c) inserting a transgene harboring a heterologous HLA allele and a homologous sequence matching the site specific recombination sequence of step b); and
    d) catalyzing said site specific recombination wherein said transgene becomes incorporated into said second chromosome by site specific recombination to provide a stem cell with altered histocompatibility phenotype.

2. The method of claim 1 wherein the catalyzing is by addition of Cre or FLP polypeptide or nucleic acid encoding the Cre or FLP polypeptide.

3. The method of claim 1 wherein the heterologous HLA allele is selected from the group consisting of HLA-B7, HLA-B8, HLA-B35, HLA-B52, HLA-B60, HLA-B44, HLA-B39, HLA-B48 and combinations thereof.

4. The method of claim 1 wherein the deleting in step a) is accomplished by transforming the cell with a knockout vector comprising a selectable marker gene and a homology sequence spanning the region 5' to the exons encoding the HLA-B MHC allele and the region 3' to the exons encoding the HLA-C MHC allele effective to remove said MHC alleles under conditions of homologous recombination.

5. The method of claim 1 wherein the replacing in step b) is accomplished by transformation with a vector comprising a homologous sequence spanning the region 5' to the exons encoding the HLA-B MHC allele and the region 3' to the exons encoding the HLA-C MHC allele and the Cre/loxP site specific recombination cassette on said second chromosome.

6. The method of claim 1 wherein the inserting step c) is accomplished with a vector comprising at least one of an MHC I HLA-B allele and a site specific recombination sequence sufficiently homologous to the site specific recombination cassette of step b) to promote site specific recombination such that at least one HLA-B allele is integrated into said second chromosome and expresses in the cell.

7. An in vitro method of altering the histocompatibility phenotype of a human stem cell, comprising:
   a) deleting MHC class II DR-B genes from a first chromosome;
   b) replacing HLA-DRB genes on a second chromosome with a site specific cassette, said cassette comprised within a vector that includes a site specific recombination sequence selected from LoxP and FRT;
   c) inserting a transgene harboring a heterologous HLA allele and a homologous sequence matching the site specific recombination sequence of step b); and
   d) catalyzing said site specific recombination wherein said transgene becomes incorporated into said second chromosome by site specific recombination to provide a stem cell with altered histocompatibility phenotype.

8. The method of claim 7 wherein the catalyzing is with addition of Cre or FLP polypeptide or nucleic acid encoding the Cre or FLP polypeptide.

9. The method of claim 7 wherein the heterologous HLA allele is selected from the group consisting of HLA-DR2, HLA-DR3, HLA-DR4, HLA-DR7, HLA-DR8, HLA-DR9, HLA-DR11, HLA-DR12, HLA-DR13, HLA-DR15, and HLA-DRBL alleles or combinations thereof.

10. The method of claim 7 wherein the deleting in step a) is accomplished by transforming the cell with a knockout vector comprising a selectable marker gene and homology sequences spanning the regions 5' and 3' to the exons encoding MHC class II DRB alleles effective to remove said MHC allele under conditions of homologous recombination.

11. The method of claim 7 wherein the replacing in step b) is accomplished by transformation with a vector comprising homologous sequences spanning the regions 5' and 3' to the exons encoding MHC class II DUR alleles and the Cre/loxP site specific recombination cassette on said second chromosome.

12. The method of claim 7 wherein the inserting step c) is accomplished with a vector comprising at least one of an MHC class II HLA-DRB allele and a site specific recombination sequence sufficiently homologous to the site specific recombination cassette of step b) to promote site specific recombination such that said at least one HLA-DUR allele is integrated into said second chromosome and expresses in the cell.

* * * * *